United States Patent
Asiri et al.

(10) Patent No.: US 11,103,595 B2
(45) Date of Patent: Aug. 31, 2021

(54) MATERIAL PRODUCTION AND APPLICATION USING AZOLE FUNCTIONALIZED NANOSILICA

(71) Applicant: Imam Abdulrahman Bin Faisal University, Dammam (SA)

(72) Inventors: Sarah Mousa Asiri, Dammam (SA); Firdos Alam Khan, Dammam (SA); Ayhan Bozkurt, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 223 days.

(21) Appl. No.: 16/380,356

(22) Filed: Apr. 10, 2019

(65) Prior Publication Data

US 2020/0323996 A1    Oct. 15, 2020

(51) Int. Cl.
  *A61K 47/54*   (2017.01)
  *A61K 47/69*   (2017.01)
  *A61P 35/00*   (2006.01)
  *B82Y 5/00*    (2011.01)

(52) U.S. Cl.
  CPC ........ *A61K 47/6923* (2017.08); *A61K 47/545* (2017.08); *A61K 47/6935* (2017.08); *A61P 35/00* (2018.01); *B82Y 5/00* (2013.01)

(58) Field of Classification Search
  CPC .............................. C07F 7/10; A61K 47/6923
  See application file for complete search history.

(56) References Cited

U.S. PATENT DOCUMENTS

| | | |
|---|---|---|
| 7,081,234 B1 | 7/2006 | Qi et al. |
| 10,947,255 B2 * | 3/2021 | Asiri |
| 2018/0334551 A1 | 11/2018 | Rodionov et al. |

FOREIGN PATENT DOCUMENTS

| | | |
|---|---|---|
| CN | 101723389 B | 12/2011 |
| CN | 106582535 A | 4/2017 |

OTHER PUBLICATIONS

Saad et al. (The Royal Society of Chemistry, pp. 57672-57682, Published 2016) (Year: 2016).*
ACS Material Advanced Chemical Supplier (Technical Data Sheet, ACS Material Mesoporous Silica Molecular Sieve SBA-15, pp. 1-5, Accessed on May 4, 2021, Accessed from https://www.acsmaterial.com/pub/media/catalog/product/t/d/tds-sba-15-20180912.pdf) (Year: 2021).*
Zhao (Science, pp. 548-552, published 1998) (Section 2.2 in the left column on p. 57674) (Year: 1998).*
A. Saad, et al., "Ligand-modified mesoporous silica SBA-15/silver hybrids for the catalyzed reduction of methylene blue" RSC Advances, Issue 62, 2016, pp. 1-4 (Abstract Only).
X. Sun, "Mesoporous silica nanoparticles for applications in drug delivery and catalysis" Graduate Theses and Dissertations, 2012, pp. 1-126.
G. Luo, et al., "Multifunctional Enveloped Mesoporous Silica Nanoparticles for Subcellular Co-delivery of Drug and Therapeutic Peptide" Scientific Reports, vol. 4, Issue 6064, Aug. 14, 2014, pp. 1-10.
M. Karakoy, et al., "Silane surface modification for improved bioadhesion of esophageal stents" Appl Surf Sci, vol. 311, 2014, pp. 684-689.

* cited by examiner

*Primary Examiner* — Alma Pipic
(74) *Attorney, Agent, or Firm* — Oblon, McClelland, Maier & Neustadt, L.L.P.

(57) ABSTRACT

A combination therapy involving different therapeutic molecules can enhance and improve the therapeutic potentials. An effective therapeutic strategy conjugates silica ($SiO_2$) nanoparticles with, e.g., 3-glycidyloxypropyl, trimethoxysilane and azoles, e.g., 1,2,4-triazole (Tri), 3-aminotriazole (ATri), 5-aminetetrazole (Atet), imidazole (Imi). These exemplary materials—classified as $SiO_2$-3GPS-Tri (Conj. 1), $SiO_2$-3GPS-Atri (Conj. 2), $SiO_2$-3GPS-Atet (Conj. 3), $SiO_2$-3GPS-Btri (Conj. 4), and $SiO_2$-3GPS-Imi (Conj. 5)—can amplify targeting of therapeutics for human colorectal carcinoma cells (HCT-116), enhancing anti-cancer effects.

12 Claims, 21 Drawing Sheets

(a)          (b)          (c)

(d)          (e)          (f)

MATERIAL PRODUCTION AND APPLICATION USING AZOLE FUNCTIONALIZED NANOSILICA

STATEMENT OF ACKNOWLEDGEMENT

The support provided by the Institute for Research & Medical Consultations (IMRC), Imam Abdulrahman Bin Faisal University, Dammam, Kingdom of Saudi Arabia, is gratefully acknowledged.

BACKGROUND OF THE INVENTION

Field of the Invention

The present disclosure relates to therapeutic agents, auxiliaries, and/or enhancers, particularly comprising a covalently bonded silica-linker-azole conjugate, particularly with a solid silica nanoparticle, which conjugate(s) may be useful, for example, for their toxicity to cancer cells and/or for enhancing chemotherapeutic value at target sites, as well as methods of making and using such conjugate(s).

Description of the Related Art

Silicon dioxide, i.e., silica, nanoparticles (SiNPs) have many applications in industrial and commercial products. Recently, SiNPs have generated tremendous interest in the field of nanomedicine wherein the use of SiNPs is broadly accepted for diagnostic imaging, drug delivery, gene therapy, and photodynamic therapy. Owing to certain beneficial attributes, SiNPs were recently named among the top five widely applied nanoparticles (NPs) by the Organization for Economic Cooperation and Development.

On the other hand, certain cytotoxicity issues have been raised for SiNPs based on in vitro studies on certain cells and tissues, however, no SiNP cytotoxicity was found in animal studies. Due these discrepancies, testing on SiNPs has continued for both in vitro and in vivo models. Initial reports on using SiNPs in cancer treatment are nonetheless encouraging, with enlarged data suggesting anti-cancer capabilities.

SiNP treatment has been reported to increase the expression of p53 and caspase 3 and decrease expression of Bcl2 and procaspase 9 in human HEPG2 hepatoma cells, while none of these effects was observed in normal human L02 hepatocytes. Another study indicates higher cytotoxicity in SiNP-treated glioblastoma cell lines. SiNP-mediated apoptosis by activating the intrinsic caspase pathway has likewise been reported.

In contrast, SiNP-dependent apoptosis was reported to be caused by death receptor-mediated pathways, and SiNPs have been reported to induce necrotic cell death. SiNPs were have been tested on brain-tumour tissue, showing that mesoporous SiNPs enhanced the radio-sensitivity of valproic acid in rat glioma, siRNA-loaded SiNPs downregulated mRNA and inducing cancer-cell death. Another report indicated that treating U87 cells with SiNPs decreased cancer cell survival.

CN 106582535 A by Wang et al. (Wang) discloses a modified silicon dioxide nanoparticle adsorbent and its preparation and application. Wang's nano silicon dioxide particles and 3-glycidyl oxypropyl trimethoxysilane are evenly mixed, added to an absolute ethyl alcohol solution, refluxed, and centrifuged to separate off a solid substance marked as GPTMS-SNPs. Wang adds these GPTMS-SNPs to an absolute ethyl alcohol solution, adds polyethyleneimine, refluxes, and centrifuges, to obtain a product marked as PEI-SNPs. Wang adds these PEI-SNPs to DMF, adds chloroacetyl chloride, refluxes, and centrifuges, to obtain a solid substance marked as CAC-SNPs. Wang mixes ethyl alcohol and water evenly, adds CAC-SNPs, then adds 3-amino-5-sulfhydryl-1,2,4-triazole, refluxes, and centrifuges, to obtain Wang's modified $SiO_2$ nanoparticle adsorbent, the structure of which is shown below.

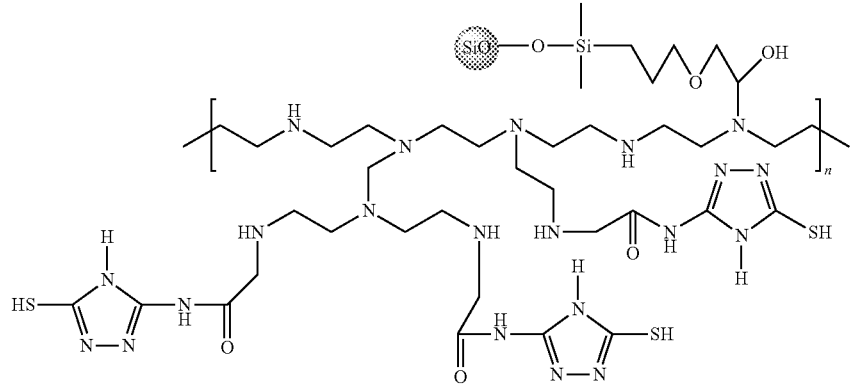

However, Wangs' product necessarily includes polyethyleneimine as an adsorbent. In addition, Wang's 1,2,4-triazole includes a mercaptan. Moreover, Wang is silent on treating cancer or using its material with therapeutics.

CN 101723389 B by Chao et al. (Chao) discloses a preparing magnetic silica microspheres that are surface-modified by cations, wherein the number of cationic electric charges varies with solution pH. Ethyl orthosilicate is hydrolyzed to generate Chao's magnetic silica microspheres by a sol-gel method in the presence of $Fe_3O_4$ nanoparticles. Chao's silica microparticles are magnetically activated with 3-glycidoxypropyl-trimethoxy silane (GPTMS), and a cationic modifying agent. Chao's magnetic silica microspheres with cationic surface-modifications are covalently bonded. Chao describes using the magnetic microspheres for separating nucleic acid from biological samples based on the variation of the electric charges on the surfaces. Chao uses histidine, polyhistidine, imidazole, 2-(N-morpholino) ethanesulfonic acid, or N,N-bis (2-hydroxyethyl)-2-aminoethanesulfonic acid for the cationic surface modification. However, Chao requires a magnetic particle, is silent on triazoles and tetrazoles, and fails to use the magnetic silica sphere for anything beyond separating amino acids, much less enhancing therapeutics or treating cancer cells.

US 2018/0334551 A1 by Rodionov et al. (Rodionov) discloses a composition of hollow spherical silica particles with outside and inside particle walls, wherein the particles have an average particle size of ~10 to 500 nm and an average wall thickness of ~10 to 50 nm; and wherein the particles are functionalized with at least one organic functional group on the outside and/or inside of the particle wall, wherein the organic functional group is in a reacted or unreacted form. Rodionov's organic functional group can be epoxy. The particles can be mixed with polymer precursor or a polymer material such as epoxy to form a prepreg or a nanocomposite. Lightweight but strong materials can be formed, and low loadings of hollow particles can be used. While Rodionov may disclose triethoxy-[3-(2-imidazolin-1-yl)-propyl]-silane and (3-glycidyloxypropyl)-trimethoxysilane as the organic functional group, as well as imidazoles as hardening agents or (co)-curing accelerators, these combinations appear to involve binding the spheres into thermoset-type polymers. Rodionov does not disclose an azole reacted with the epoxide group of, e.g., (3-glycidyloxypropyl)-trimethoxysilane, nor does Rodionov disclose combining its substances with or as therapeutics, particularly not for anticancer therapy.

U.S. Pat. No. 7,081,234 to Qi et al. (Qi) discloses a treating metal oxide nanoparticles including mixing metal oxide nanoparticles, a solvent, and a surface treatment agent that is preferably a silane or siloxane. Qi's metal oxides may be alumina, titania, zinc oxide, iron oxide, silica, ceria, chromium oxide, zirconia, tin oxide, magnesia, manganese oxide, nickel oxide, copper oxide, and/or indium tin oxide. Qi's treated metal oxide nanoparticles are rendered hydrophobic by the surface treatment agent being surface attached thereto, and are preferably dispersed in a hydrophobic aromatic polymer binder of a charge transport layer of a photoreceptor, whereby π-π interactions can be formed between the organic moieties on the surface of the nanoparticles and the aromatic components of the binder polymer to achieve a stable dispersion of the nanoparticles in the polymer that is substantially free of large sized agglomerations. Qi may use diamines, aromatic amines, pyrazolines, substituted fluorenes, oxadiazoles, hydrazones, carbazole phenyl hydrazones, tri-substituted methanes and mixtures thereof, including, e.g., pyrazoline, imidazole, triazole, as a charge transport molecule, but does not bond the charge transport molecule to the metal oxide particle, particularly not via a particular organosilane epoxide. Qi likewise fails to disclose using its particles in or as therapeutic agents, particularly not in connection with treating cancers.

*RSC Adv.* 2016, 62, 57672-57682 by Saad et al. (Saad) discloses mesoporous silica SBA-15 functionalized by (3-glycidyloxypropyl)trimethoxysilane in order to bind 2-aminothiazole and aminopropyl-triazole ligands. These groups were immobilized through two distinct chemistry routes: (i) reaction of epoxy with amine resulting in AMT-SBA-15 for the former, and (ii) epoxy ring opening followed by 1,3-dipolar cycloaddition click reaction providing Tr-SBA-15, obtaining the structures as indicated below:

Tr-SBA-15 and

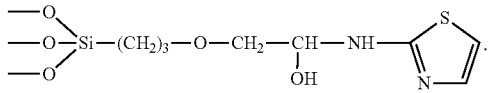

AMT-SBA-15

Saad's ligand-functionalized SBA-15 materials served as reactive platforms for the in situ deposition of silver nanoparticles from the reduction of silver nitrate. Saad's silver-decorated hybrid Ag/AMT-SBA-15 and Ag/Tr-SBA-15 samples were evaluated as catalysts for the reduction of methylene blue. However, Saad uses only a 1,2,3-triazole and a 1,3-thiazole and does not disclose hollow silica nanoparticles. Further, Saad's compounds are not used as and/or in combination with therapeutics and/or medicines, particularly not against cancer cells.

The 2012 doctoral thesis from Iowa State University, entitled "Mesoporous Silica Nanoparticles for Applications in Drug Delivery and Catalysis," by Xiaoxing Sun (Sun) discloses tethering a Pt(II) bipyridine catalyst onto organo-functionalized hybrid mesoporous silica nanoparticles (MSNs) in order to enhance its thermal stability and product selectivity. Sun shows that catalytic performance was similar between the homogeneous and heterogeneous systems, though the homogeneous system exhibited appreciable degradation after 16 hours at 100° C. Sun describes that MSN scaffolds allow the catalyst system to retain its activity after 72 hours at 150° C. Sun describes a biocatalyst to function synergistically with MSN supported inorganic catalysts in that a supported Au-nanoparticle catalyst for direct alcohol oxidative esterification usually suffers from a slow alcohol oxidation rate, but a co-catalyst system combining an alcohol dehydrogenase and Au-nanoparticle catalyst accelerates the reaction. Sun describes intracellular co-delivery of a biocatalyst on a gold nanoparticle-capped MSN platform by releasing luciferin from the interior pores of MSNs upon gold nanoparticle uncapping in response to disulfide-reducing antioxidants, and co-delivery of bioactive luciferase from the PEGylated exterior surface of MSNs into Hela cells. Sun describes that the co-delivery systems could play a role in intracellular controlled catalysis and tumor imaging. However, Sun does not describe solid silicon dioxide nanoparticles surface modified with (3-glycidyloxypropyl)-trimethoxysilane and an azole, particularly wherein the silicon of (3-glycidyloxypropyl)-trimethoxysilane forms a covalent bond to the oxygen atoms of the silicon dioxide and the azole forms a covalent adduct with the oxirane ring of (3-glycidyloxypropyl)-trimethoxysilane.

*Sci. Rep.* 2014, 4, 6064-1-10 by Luo et al. (Luo) discloses a multifunctional enveloped nanodevice based on mesoporous silica nanoparticle (MSN) designed for subcellular co-delivery of drug and therapeutic peptide to tumor cells. Mesoporous silica MCM-41 nanoparticles were used as the core for loading the antineoplastic drug topotecan (TPT). The surface of Luo's nanoparticles was decorated with mitochondria-targeted therapeutic agent (Tpep) containing triphenylphosphonium (TPP) and antibiotic peptide (KLAKLAK)2 via disulfide linkage, followed by coating with a charge reversal polyanion poly(ethylene glycol)-blocked-2,3-dimethylmaleic anhydride-modified poly(L-lysine) (PEG-PLL(DMA)) via electrostatic interaction. Luo finds that the outer shielding layer could be removed at acidic tumor microenvironment due to the degradation of DMA blocks and the cellular uptake was significantly enhanced by the formation of cationic nanoparticles. After endocytosis, due to the cleavage of disulfide bonds in the presence of intracellular glutathione (GSH), pharmacological agents (Tpep and TPT) could be released from the nanoparticles and subsequently induce specific damage of tumor cell mitochondria and nucleus respectively with remarkable synergistic antitumor effect. Luo does not disclose solid silicon nanoparticles modified with an azole.

*Appl. Surf Sci.* 2014, 311, 684-689 by Krakoy et al. (Krakoy) discloses that stent migration occurs in 10 to 40% of patients who undergo placement of esophageal stents, with higher migration rates seen in those treated for benign esophageal disorders. Krakoy propose a new surface modification method to increase the adhesion between self-expandable metallic stents (SEMS) and tissue while preserving their removability. Krakoy modifies the surfaces of silicone coated esophageal SEMS with adhesive self-assembled monolayers (SAMs) using vapor phase silanization to modify the surfaces of different substrates including PDMS strips and SEMS. Krakoy states that surface modification of esophageal SEMS via covalent attachment of protein-binding coupling agents improves adhesion to tissue and could offer a solution to reduce SEMS migration while preserving their removability. Krakoy discloses a trialkoxysilyl epoxide or amine bonded to its silicone coating upon the stents, but fails to mention silica nanoparticles or azoles.

While promising data is available on the effect of SiNPs on cancer cells, there is still a need for agents that demonstrate and model the therapeutic potential of SiNPs, particularly as conjugates with (3-glycidyloxypropyl) trimethoxysilane and azoles, for example, as auxiliaries for treating cancer cells, such as in enhancing the cytotoxicity and/or targeting of chemotherapeutics, and methods of making and using such SiNP agents.

SUMMARY OF THE INVENTION

Aspects of the invention provide conjugates, comprising: a silicon dioxide nanoparticle surface modified with a linker of Formula (1)

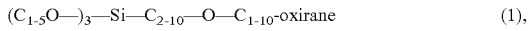
$$(C_{1-5}O-)_3-Si-C_{2-10}-O-C_{1-10}\text{-oxirane} \qquad (1),$$

and an azole, wherein the nanoparticle comprises at least 85 wt. % silica, based on total nanoparticle weight, wherein the silicon of linker forms a covalent bond to the oxygen atoms of the silicon dioxide, and wherein the azole forms a covalent bond with a carbon atom of the oxirane via ring-opening of the oxirane of the linker. Such conjugates can be modified with any permutation of the features described herein, particularly the following.

The nanoparticle size may be in a range of 5 nm to 60 nm.
The azole may be 1,2,4-triazole, 3-amino-1,2,4-triazole, 5-aminotetrazole, 1H-benzotriazole, or imidazole.
The nanoparticles may be non-magnetic.
The nanoparticles comprise at least 97.5 wt. % silica, relative to the total nanoparticle weight.
Inventive conjugate may enhance cell death of cancer cells exposed to the conjugate, at least 50% relative to a placebo within 48 hours of exposure.
The cancer cells comprise HCT-116 cells.
The linker of Formula (1) may have Formula (1a):

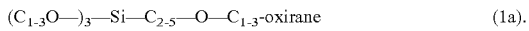
$$(C_{1-3}O-)_3-Si-C_{2-5}-O-C_{1-3}\text{-oxirane} \qquad (1a).$$

The linker may comprise, in reacted form, (3-glycidyloxypropyl)-trimethoxysilane and/or (3-glycidyloxypropyl)-triethoxysilane.
The nanoparticles may have a density in a range of from 2 to 3 (2.2 to 2.6) g/mL at 25° C.

The nanoparticles have a bulk density in a range of from 0.008 to 0.015 (0.011) g/mL.

Aspects of the invention include therapeutic agents, comprising: at least 50 wt. % of one or more of the inventive conjugates described herein relative to total agent weight, wherein the agent is suitable to enhance cell death of cancer cells exposed to the agent, at least 50% relative to a placebo.

Aspects of the invention provide methods of preparing any inventive conjugate as described herein, wherein such methods may comprise: reacting a linker of Formula (1)

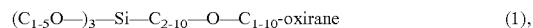
$$(C_{1-5}O-)_3-Si-C_{2-10}-O-C_{1-10}\text{-oxirane} \qquad (1),$$

with an azole, to obtain a first product; mixing the first product with silicon dioxide nanoparticles to obtain a mixture, the nanoparticles having an average diameter in a range of from 5 to 60 nm and a silicon dioxide content of at least 75 wt. %, relative to total nanoparticle weight; and heating the mixture at a temperature in a range of from 50 to 90° C.

The linker may comprise, in reacted form, (3-glycidyloxypropyl)-trimethoxysilane and/or (3-glycidyloxypropyl)-triethoxysilane. The reacting may occur in an alcohol at a temperature in a range of from 60 to 120° C., for a time period in a range of from 2 to 6 hours. Prior to the heating, the pH of the mixture may be made basic.

Aspects of the invention provide methods of bringing about cancer cell death, the method comprising: exposing cancer cells to a 1 to 10 mg/mL solution of one or more of the inventive conjugates described herein for a period of no more than 96 hours, thereby reducing a cancer cell survival rate to no more than 50% the amount of a control.

Inventive methods may enhance cell death of cancer cells exposed to the conjugate, at least 50% relative to a placebo within 48 hours of exposure. The cell death may arise from nuclear condensation, nuclear augmentation, and/or cell membrane disruption.

Aspects of the invention include methods of treating cancer, comprising: administering to a patient in need thereof an effective amount of one or more of any of the inventive conjugates described herein.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
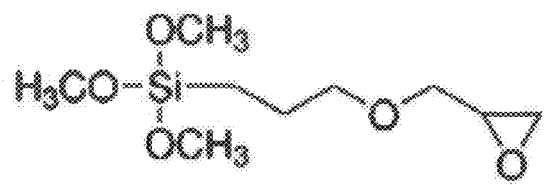
FIG. 1 shows schematic representations of (a) 3-glycidyloxypropyl trimethoxysilane, (b) 1,2,4-triazole, (c) 3-amino-1,2,4-triazole, (d) 5-aminotetrazole monohydrate, (e) 1H-benzotriazole, and (f) imidazole.
Figure 1:
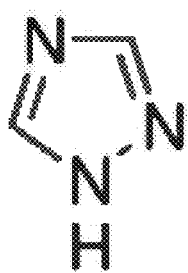
Figure 1:
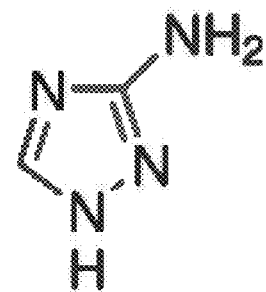
Figure 1:
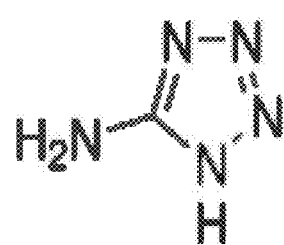
Figure 1:
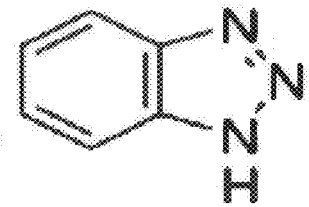
Figure 1:
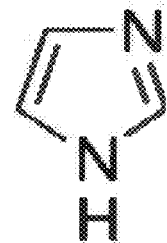

Aspects of the invention provide conjugates comprising, in reacted form, a preferably solid silicon dioxide nanoparticle that is surface modified with a linker, which, prior to reaction into the conjugate, has a Formula (1)

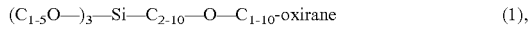

$$(C_{1-5}O—)_3—Si—C_{2-10}—O—C_{1-10}\text{-oxirane} \quad (1),$$

and an azole, wherein the nanoparticle comprises at least 85, 90, 91, 92, 92.5, 93, 94, 95, 96, 97, 97.5, 98, 99, 99.1, 99.5, or 99.9 wt. % silica, based on total nanoparticle weight, wherein, in reacted form, the silicon of the linker forms a covalent bond to at least one oxygen atom of the silicon dioxide of the silica, with the alkyloxysilane, $(C_{1-5}O—)_3—Si—$, of the linker shedding an alkoxyl group, e.g., as an alcohol, and wherein the azole forms a covalent bond with a carbon atom of the (opened) oxirane via ring-opening of the oxirane of the linker with the azole, as an optionally substituted hydroxymethine-methylene-azole unit, e.g., to $—CH(OH)—CH_2—$, optionally having one or more hydrogens replaced by a C1, C2, C3, C4, or C5 group which may be interrupted by O, S, N, or P.

Examples of useful linkers (prior to reaction to form the conjugate), besides the 3-glycidyloxypropyl trimethoxysilane exemplified below may be, for example, 3-glycidyloxypropyl trimethoxysilane, 3-glycidyloxypropyl triethoxysilane, 3-glycidyloxypropylmethyl dimethoxysilane, 3-glycidyloxypropylmethyl diethoxysilane, 3-glycidyloxypropyldimethyl methoxysilane, 3-glycidyloxypropyldimethyl ethoxysilane, 2-glycidyloxyethyltrimethoxysilane, 2-glycidyloxyethyl triethoxysilane, 2-glycidyloxyethylmethyl dimethoxysilane, 2-glycidyloxyethylmethyl diethoxysilane, 2-glycidyloxyethyldimethyl methoxysilane, 2-glycidyloxyethyldimethyl ethoxysilane, 4-glycidyloxybutyl trimethoxysilane, 4-glycidyloxybutyl triethoxysilane, 4-glycidyloxybutylmethyl dimethoxysilane, 4-glycidyloxybutylmethyl diethoxysilane, 4-glycidyloxybutyldimethyl methoxysilane, 4-glycidyloxybutyldimethyl ethoxysilane, 2-(3,4-epoxycyclohexyl)ethyl trimethoxysilane, 2-(3,4-epoxycyclohexyl)ethyl triethoxysilane, 3-(3,4-epoxycyclohexyl)propyl trimethoxysilane, 3-(3,4-epoxycyclohexyl)propyl triethoxysilane, [(3-ethyl-3-oxetanyl)methoxy]

propyl trimethoxysilane, [(3-ethyl-3-oxetanyl)methoxy]propyl triethoxysilane, [(3-ethyl-3-oxetanyl)-methoxy]-propylmethyldimethoxysilane, and [(3-ethyl-3-oxetanyl)-methoxy]-propyl-dimethyl-dimethoxysilane. Useful general structures may involve an trialkoxysilyl moiety (e.g., methoxy, ethoxy, propoxy, C4-O—, C5-O—, etc.) covalently bonded to a C2 to C10 (e.g., C3, C4, C5, C6, C7, C8, or C9) alkyl group optionally interrupted by 1, 2, or 3 oxygen atoms, covalently bonded to an O—C1 to O—C10 (e.g., C2, C3, C4, C5, C6, C7, C8, or C9) alkyl group, covalently bonded to an oxirane (i.e., epoxide), as follows:

$$(C_{1-5}O-)_3-Si-C_{2-10}-O-C_{1-10}\text{-oxirane}.$$

The unreacted linker of Formula (1) may have Formula (1a), (1b), (1c), or (1d):

$$(C_{1-3}O-)_3-Si-C_{2-7}-O-C_{1-4}\text{-oxirane} \quad (1a),$$

$$(C_{1-2}O-)_3-Si-C_{2-5}-O-C_{1-3}\text{-oxirane} \quad (1b),$$

$$(C_{1-2}O-)_3-Si-C_{2-4}-O-C_{1-2}\text{-oxirane} \quad (1c), \text{ or}$$

$$(C_{1-2}O-)_3-Si-C_{2-3}-O-C_1\text{-oxirane} \quad (1d).$$

Of course, the alkyl groups, such as "$C_{1-5}$" or "$C_1$" or the like, as set forth herein, will be further substituted to fill the valences, generally with —H, but optionally with non-reactive components in the conjugation system, such as —F, —OMe, —CH$_3$, —CH$_2$CH$_3$, etc. Functional groups and/or branching may be used to tailor the solubility and/or bioavailability of the conjugates. The linker may preferably comprise, in reacted form, (3-glycidyloxypropyl)-trimethoxysilane and/or (3-glycidyloxypropyl)-triethoxysilane.

Examples of useful azoles, prior to reaction into the conjugate, may include, for example, imidazole, pyrazole, 1,2,3-triazole, 1,2,4-triazole, tetrazole, oxazole, isoxazole, 1,2,4-oxadiazole, 1,2,5-oxadiazole, 1,3,4-oxadiazole, thiazole, isothiazole, 1,2,3-thiadiazole, 1,2,4-thiadiazole, 1,2,5-thiadiazole, 1,3,4-thiadiazole, a functionalized analog of any of these, or mixtures of two or more of any of these. Functional groups on these azoles may include an azide, amine, nitrile, isonitrile, isocyanate, thiocyanate, isothiocyanate, nitro, nitroso, thiol, thioether, fluoride, chloride, bromide, or iodide, hydroxyl, methyl, ethyl, n-propyl, isopropyl, n-butyl, iso-butyl, sec-butyl, vinyl, $C_3$ alkenyl group, $C_4$ alkenyl group, $C_5$ alkenyl group, OCH$_3$, OCH$_2$CH$_3$, OCH$_2$CH$_2$CH$_3$, OCH(CH$_3$)$_2$, OCH$_2$CH$_2$CH$_2$CH$_3$, isobutoxy, sec-butoxy, methoxymethyl, methoxyethyl, ethoxymethyl, (hetero)aryl ether (meaning heteroaryl or aryl), $C_1$-$C_5$ carboxylate, $C_{0-05}$ sulfonate, $C_1$-$C_{10}$ amide C(O)N or reverse amide NC(O), $C_1$-$C_{10}$ ester C(O)O or reverse ester OC(O), $C_0$-$C_{10}$ (reverse) sulfonamide, and/or $C_0$-$C_{10}$ (reverse) sulfonic ester. Typically, the azole will include no more than one functional group, though 2 or 3 may be functionalizations may be present as feasible, depending upon the application. The azole may preferably include a 1,2,4-triazole, 3-amino-1,2,4-triazole, 5-aminotetrazole, 1H-benzotriazole, imidazole, or mixture of two or more of any of these.

The nanoparticle size, i.e., average particle diameter, may be in a range of 5 to 100, 10 to 90, 20 to 80, 30 to 70, 40 to 60, about 50, 6 to 40, 8 to 30, or 10 to 20 nm. The nanoparticles may have a density in a range of from 2 to 3, 2.05 to 2.9, 2.1 to 2.8, 2.15, to 2.7, 2.2 to 2.6, or 2.25 to 2.5 g/mL at 25° C. The nanoparticles have a bulk density in a range of from 0.008 to 0.015, 0.009 to 0.014, 0.0095 to 0.013, 0.010 to 0.012, 0.0105 to 0.0115, or 0.011 g/mL. Inventive conjugates generally comprise no more than trace, if any Fe$_3$O$_4$ (or Fe) or no more than 15, 10, 7.5, 5, 4, 3, 2, 1, 0.5, 0.1, 0.01, 0.001, or 0.0001 wt. % Fe$_3$O$_4$ (or Fe), relative to the total weight of the silica microspheres and/or the conjugate. Inventive conjugates are generally non-ferromagnetic and/or non-magnetic. The nanoparticles may be non-magnetic.

Inventive conjugates may enhance cell death of cancer cells exposed to the conjugate, at least 50, 45, 40, 35, 33.3, 30, 27.5, 25, 22.5, 20, 17.5, 16.7, 15, 13.3, 12.5, 10, 7.5, 5, or 2.5% relative to a placebo within 96, 72, 48, 36, 24, 20, or 16 hours of exposure. The cancer cells comprise HCT-116 cells. Potential cancer cells for treatment include human, canine, murine, bovine, equine, and feline cells. Carcinoma (e.g., basal cell, ductal carcinoma, renal cell, merkel cell carcinoma, squamous cell carcinoma, etc.), sarcoma (e.g., leiomyosarcoma, Kaposi sarcoma, malignant fibrous histiocytoma, liposarcoma, Ewing sarcoma, osteosarcoma, dermatofibrosarcoma protuberans, etc.), leukemia (chronic lymphocytic leukemia (CLL), chronic myelogenous leukemia (CML), etc.), lymphoma (Hodgkin and/or non-Hodgkin lymphoma, cutaneous T-cell lymphoma, etc.), multiple myeloma, and/or melanoma afflicted cells may be subject to treatment with inventive conjugates. Cancer cells affected may be derived from human cancer cell lines, such as colon cancer cell lines, e.g., HCT15, MDST8, GP5d, HCT116, DLD1, HT29, SW620, SW403, and/or T84; liver cancer cell lines, e.g. HepG2, PLC/PRF/5, THLE-3, C3A, SNU-182, SNU-398, SNU-387, SNU-423, SNU-475, SNU-449, and/or Hep 3B2.1-7; lung cancer cell lines, e.g., A549, SHP-77, COR-L23/R, and/or NCI-H69/LX20; breast cancer cell lines, e.g., MDA-MB-231, MCF7, T47D, and/or VP303; cervical cancer cell lines, e.g., HeLa DH, HtTA-1, HR5, and/or C-4I; ovarian cancer cell lines, e.g., A2780, A2780cis, OV7, and/or PE023; and/or skin cancer cell lines, e.g., C32TG, A375, and/or MCC26. The cancer cells may be collected from a human patient at risk of having, suspected of having, diagnosed with, or being monitored for recurrence of at least one type of cancer, e.g., colon cancer, liver cancer, and/or lung cancer.

Cytotoxically effective amounts of active ingredient including the conjugate(s) and optionally further active agents may be amounts that reduce the viability of the cancer cells by at least 5, 10, 15, 20, 30, 40, 50, 60, 70, 80, or 90%, relative to cancer cells not treated with the active ingredient. The reduction in viability may occur within 10, 7, 5, 3, 2, 1, or 0.5 days after the active ingredient is contacted with the cancer cells. The cytotoxic effective amount may be an IC$_{50}$ which is a concentration of the active ingredient which causes the death of 50% of cancer cells in 24±1, 2, 4, or 8 hours (roughly 1 day). The IC$_{50}$ against colon cancer cells may be in a range of 0.1 to 100, 1 to 50, or 10 to 20 μM. The IC$_{50}$ against liver cancer cells may be in a range of 0.01 to 50, 0.1 to 25, or 1 to 10 μM. The IC$_{50}$ against lung cancer cells may be in a range of 0.01 to 40, 0.1 to 20, or 4 to 8 μM.

Inventive conjugate(s) may be incorporated into pharmaceutical compositions including a second (third, fourth, or further) active ingredient, such as a chemotherapeutic agent or an anticancer agent, for the treatment or prevention of neoplasm, of tumor or cancer cell division, growth, proliferation and/or metastasis in the subject; induction of death or apoptosis of tumor and/or cancer cells; and/or any other forms of proliferative disorder.

Exemplary further active ingredients may include a mitotic inhibitor, an alkylating agent, an antimetabolite, a cell cycle inhibitor, a topoisomerase inhibitor, a biological response modifier, an anti-hormone, an antiangiogenic agent (e.g., MMP-2, MMP-9 and COX-2 inhibitor), an anti-androgen, a platinum coordination complex (e.g., oxaliplatin, cis-platin, carboplatin), a substituted urea such as hydroxyurea, a methylhydrazine derivative, an adrenocortical suppressant (e.g., mitotane, aminoglutethimide), a hormone and/or hormone antagonist such as the adrenocorticosteriods (e.g., prednisone), progestins (e.g., hydroxyprogesterone caproate), an estrogen (e.g., diethylstilbestrol); an antiestrogen such as tamoxifen; androgen (e.g., testosterone propionate), an aromatase inhibitor (e.g., anastrozole, and AROMASIN (exemestane)), or combinations of two or more of any of these.

Useful anticancer agents may include, e.g., alkylating antineoplastic agents including busulfan, carmustine, chlorambucil, cyclophosphamide, cyclophosphamide, dacarbazine, ifosfamide, lomustine, mechlorethamine, melphalan, mercaptopurine, and/or procarbazine; antimetabolites including cladribine, cytarabine, fludarabine, gemcitabine, pentostatin, 5-fluorouracil, clofarabine, capecitabine, methotrexate, and/or thioguanine; anti-microtubule agents including etoposide, vinblastine, vincristine, teniposide, docetaxel, paclitaxel, vinorelbine, and/or vindesine; cytotoxic antibiotics including daunorubicin, doxorubicin, idarubicin, mitomycin, actinomycin, and/or epirubicin; topoisomerase inhibitors including irinotecan, mitoxantrone, and/or topotecan; or mixtures of these.

Useful pharmaceutically acceptable carriers and formulations thereof are described in, e.g., Remington's Pharmaceutical Sciences, 21st Edition, ed. University of the Sciences in Philadelphia, Lippincott, Williams & Wilkins, Philadelphia Pa., 2005, and Liberman, H. A.; Lachman, L., Eds. Pharmaceutical dosage forms, Marcel Decker, New York, N.Y., 1980, each of which is incorporated herein by reference in its entirety. Liquid dosage forms for oral administration may include pharmaceutically acceptable emulsions, solutions, suspensions, syrups, and elixirs containing inert diluents commonly used in the art, such as water. Compositions may comprise adjuvants, sweetening, flavor, and/or scent ingredients. Parenteral formulations may be aqueous or non-aqueous, isotonic, sterile injection solutions or suspensions suitable for intravenous, intravesical, intraperitoneal, subcutaneous, intramuscular, intralesional, intracranial, intrapulmonal, intracardial, intrasternal, and/or sublingual injection, and/or infusion techniques. Useful parenterals may be prepared from sterile powders or granules optionally including known carrier(s) and/or diluent(s). Further administration forms may include suppositories and/or topical forms for transdermal administration.

Aspects of the invention include therapeutic agents, comprising: at least 50 wt. % of one or more of the inventive conjugates described herein relative to total agent weight, wherein the agent is suitable to enhance cell death of cancer cells exposed to the agent, at least 50% relative to a placebo.

Aspects of the invention provide methods of preparing any inventive conjugate as described herein, wherein such methods may comprise: reacting a linker of Formula (1), (1a), (1b), (1c), or (1d) with an azole, to obtain a first product; mixing the first product with solid silicon dioxide nanoparticles to obtain a mixture, the nanoparticles having an average diameter in a range of from 5 to 60 nm (e.g., at least 2, 4, 6, 8, 10, 12, or 15 nm, and/or no more than 100, 75, 65, 55, 45, 40, 35, 30, 25, 20, or 15 nm) and a silicon dioxide content of at least 75, 85, 90, 92.5, 95, or 97.5 wt. %, relative to total nanoparticle weight; and heating the mixture at a temperature in a range of from 50 to 90, 60 to 80, 65 to 75, 67.5 to 72.5, or 70±1, 2, 2.5, 3, 4, or 5° C.

The unreacted linker of the conjugate may comprise, in reacted form, (3-glycidyloxypropyl)-trimethoxysilane and/or (3-glycidyloxypropyl)-triethoxysilane and/or any of other linker(s) described herein. The reacting may occur in an alcohol or other solvent(s) at a temperature in a range of from 60 to 120, 70 to 100, 75 to 90, 77.5 to 85, or 80° C., for a time period in a range of from 2 to 6, 2.5 to 4, 2.75 to 3.5, or 3 hours±3, 6, 9, 12, or 15 minutes. Prior to the heating, the pH of the mixture may be made basic, particularly, bringing the pH above 7.5, 8, 8.5, 9, 9.5, or 10 and/or no more than 13, 12.5, 12, 11.5, 11, 10.5, or 10. Useful solvents may include pyridine, N,N-dimethylformamide (DMF), N,N-dimethylacetamide, N-methyl pyrrolidone (NMP), hexamethylphosphoramide (HMPA), dimethyl sulfoxide (DMSO), acetonitrile, tetrahydrofuran (THF), 1,4-dioxane, dichloromethane, chloroform, carbon tetrachloride, dichloroethane, acetone, ethyl acetate, pet ether, pentane, hexane(s), decalin, THF, dioxane, toluene, xylene(s), o-dichlorobenzene, diethyl ether, methyl t-butyl ether, methanol, ethanol, ethylene glycol, isopropanol, propanol, n-butanol, and/or water.

Aspects of the invention provide methods of bringing about cancer cell death, the method comprising: exposing cancer cells to a 1 to 10, 1.25 to 8, 1.5 to 7.5, 2.5 to 7, or 3.5 to 6.67 mg/mL solution of one or more of the inventive conjugates described herein for a period of no more than 96, 84, 72, 60, 48, 36, 30, 24, 20, or 18 hours, thereby reducing a cancer cell survival rate to no more than 45, 40, 35, 33.3, 30, 27.5, 25, 22.5, 20, 17.5, 16.7, 15, 13.3, 12.5, 10, 7.5, 5, or 2.5% the amount of a control. The solution may be a growth medium, or may be an organic solution.

Inventive methods may enhance cell death of cancer cells exposed to the conjugate, at least 40, 35, 33, 30, 27.5, 25, 22.5, 20, 17.5, 15, 12.5, 10, 7.5, 5, 4, 3, 2, 1, or 0.5% relative to a placebo within 48, 44, 40, 36, 32, 28, 24, 22, 20, 18, 16, 14, or 12 hours of exposure. The cell death may arise from nuclear condensation, nuclear augmentation, and/or cell membrane disruption.

Aspects of the invention include methods of treating cancer comprising administering to a patient in need thereof an effective amount of one or more of any of the inventive conjugates described herein. The cancer may be any as described herein, such as an epithelial cell (e.g., squamous cell, adeno cell—breast, bowel, stomach, ovaries and prostate, urothelial (transitional) cell, basal cell, etc.), blood cell, lymph cell, or connective tissue cell cancer. The patient may be an adult patient, preferably human, though also bovine, equine, canine, feline, murine, Sus domesticus, or the like. The dosage may be in a range of from 1 to 1000, 2 to 500, 3 to 400, 4 to 300, 5 to 250, 7.5 to 125, 10 to 100, or 12.5 to 50 mg/kg, though the dosage may be no more than 1000, 750, 500, 250, 200, 150, 100, 75, 50, 25, 20, 15, 10, 5, or 1 ng/kg, depending upon the sensitivity of the organism. The dosage regimen may involve a 6, 8, 12, or 24-hourly frequency, e.g., for 2, 3, 4, 5, 6, or more weeks. The manner of administration may be, for example, oral or intravenous (e.g., subcutaneous).

A composition or "pharmaceutical" composition comprising one or more inventive conjugates may be a mixture of the active ingredient with other chemical components, such as pharmaceutically acceptable carriers and excipients. A composition may facilitate administration of the inventive conjugate(s) to a subject/patient. Pharmaceutical compositions may be manufactured by processes well known in the art, e.g., by conventional mixing, dissolving, granulating, dragee-making, levigating, emulsifying, encapsulating, entrapping, or lyophilizing. Depending on the intended mode of administration (e.g., oral, parenteral, or topical), compositions can be in solid, semi-solid, and/or liquid dosage forms, such as tablets, suppositories, pills, capsules, powders, liquids, or suspensions, generally in unit dosage form suitable for single administration of a precise dosage. Pharmaceutical compositions may comprise up to 0.01, 0.1, 1, 5, or 10 wt. % of the pharmaceutically acceptable carrier(s) and/or excipient(s) relative to a total weight of the pharmaceutical composition. Pharmaceutical compositions may comprise at least 0.01, 0.05, 0.1, 0.5, 5, 10, 15, 20, 25, 30, 35, 40, 45, 50, 55, 60, 65, 70, 75, 80, 85, 90, 95, 99, or 99.9 wt. % of the inventive conjugate(s).

Conjugates within the scope of the invention, salt(s), solvate(s), tautomer(s), stereoisomer(s), and/or mixtures thereof, may act as anticancer agent(s) in reducing the viability of cancer cells derived from human cancer cell lines including, but not limited to, colon cancer cell lines (e.g. HCT-116, HT-29), liver cancer cell lines (e.g. HepG2), lung cancer cell lines (e.g. A549, NCI-H460), breast cancer cell lines (e.g. MCF-7, and SK-BR-3), brain tumor cell lines (e.g. U251), ovarian cancer cell lines (e.g. NCI-ADR/RES, OVCAR-03), prostate cancer cell lines (e.g. PC-3), renal cancer cell lines (e.g. 786-0), and/or melanoma cell lines (e.g. UACC-62). Non-cancerous proliferative disorders may also be treated by inventive conjugates such as, without limitation, atherosclerosis, rheumatoid arthritis, psoriasis, idiopathic pulmonary fibrosis, scleroderma, cirrhosis, lymphoproliferative disorder, other disorders involving epidermal cell proliferation such as verruca (warts), and/or dermatitis. Inventive conjugates may exhibit therapeutic activities such as antimicrobial (e.g. antibacterial, antifungal, antiviral, antimycobacterial), antimalarial, pesticidal, antioxidant, and/or anti-inflammatory efficacies.

Aspects of the invention include therapeutic conjugates of nanoparticles comprising, for example, silica ($SiO_2$), bonded to an azole, for example 1,2,4-triazole (Tri), 3-aminotriazole (ATri), 5-aminetetrazole (Atet), imidazole (Imi), using a trimethoxysilane, e.g., 3-glycidyloxypropyl trimethoxysilane (3GPS). Exemplary materials—classified as $SiO_2$-3GPS-Tri (Conj. 1), $SiO_2$-3GPS-Atri (Conj. 2), $SiO_2$-3GPS-Atet (Conj. 3), $SiO_2$-3GPS-Btri (Conj. 4), and $SiO_2$-3GPS-Imi (Conj. 5)—can amplify targeting of therapeutics for human colorectal carcinoma cells (HCT-116), enhancing anti-cancer effects. Inventive materials can decrease cell viability, cell proliferation, and cause cell death in a concentration-dependent manner within 48, 44, 40, 36, 32, 28, or even 24 hours. The conjugates can increase cytotoxic effects on cancer cells, possibly by nuclear disintegration, augmentation, and fragmentation.

Aspects of the invention provide conjugated SiNPs, for example, with 3-glycidyloxypropyl trimethoxysilane and different azoles groups such as 1,2,4-triazole (Tri), 3-amino-triazole (ATri), 5-amino-tetrazole (Atet), imidazole (Imi), and tested their use on cancer cells, e.g., at different concentrations and/or different exposure periods, such as 24 or 48 hour-treatments.

Inventive conjugates are generally neutral, or uncharged, though depending upon the application, they may be negatively charged, positively charged, or zwitterionic. If cationic, inventive conjugates will generally have no more than 5, 4, 3, 2, or 1 charge. Depending upon the application, however, further cationic charges may be implemented. The charges on the inventive conjugates need not be pH dependent.

Inventive conjugates generally comprise no more than trace, if any histidine or no more than 15, 10, 7.5, 5, 4, 3, 2, 1, or 0.5 wt. % histidine, relative to the total weight of N-heterocyclic rings. Useful azoles are generally unlimited, but may exclude thiol groups, particularly thiol groups connected to the aromatic ring. The azoles may be functionalized as described herein, but are generally not bonded to polynucleotides, such as DNA or RNA, and/or polypeptides, such as proteins, antibodies, enzymes, etc. The azoles may exclude 1,2,3-triazoles and/or 1,3-thiazoles.

The surface of inventive silica particles generally contain less than 10, 5, 2.5, 1, 0.5, 0.1, 0.01, 0.001, or 0.0001 wt. % triphenylphosphonium, relative to all coatings on the particles. The surface of inventive silica particles generally contain less than 10, 5, 2.5, 1, 0.5, 0.1, 0.01, 0.001, or 0.0001 wt. % polynucleotides and/or polypeptides, esp. (KLAKLAK)2, and/or polyalkylene oxides, esp. PEG-PLL(DMA).

Inventive conjugates may comprise no more than 40, 33, 25, 20, 15, 10, 7.5, 5, 4, 3, 2, 1, 0.5, 0.1, 0.01, or 0.001 wt. %, relative to the total conjugate weight, of polyethyleneimine, or may avoid polyethyleneimines entirely (beyond any inevitable traces).

Any therapeutic combination including the conjugate and one or more drugs may preferably have no more than 10, 5, 2.5, 1, 0.5, 0.1, 0.01, 0.001, or 0.0001 wt. % topotecan, based on the mass of active pharmaceuticals in the combination.

EXAMPLES

CHEMICALS: Silicon dioxide $SiO_2$ (silica) nanoparticles (10-20 nm particle size, 99.5%) (3-glycidyloxypropyl) trimethoxysilane ($C_9H_{20}O_5Si$, ≥98%, MW: 236.34 g/mol), 1,2,4-triazole ($C_2H_3N_3$, 98%, MW: 69.07 g/mol), 3-amino-1,2,4-triazole ($C_2H_4N_4$, ≥95%, MW: 84.08 g/mol), 5-aminotetrazole monohydrate ($CH_3N_5 \cdot H2O$, ≥97%, MW: 103.08·g/mol), 1H-benzotriazole ($C_6H_5N_3$, ≥99%, MW: 119.12 g/mol), imidazole ($C_3H_4N_2$, ≥99%, MW: 68.077 g/mol), shown in FIG. 1 (a, b, c, d, e, and f), and sodium hydroxide (NaOH) were obtained from Sigma-Aldrich and used as precursors without further purification.

NANOPARTICLE AND CONJUGATE SYNTHESIS: Equimolar amounts of (0.5 g, 2.1155 mmol) of (3-glycidyloxypropyl)-trimethoxysilane (3GPS) were mixed with 0.14 g (2.0269 mmol) of 1,2,4-triazole (Tri), 0.176 g (2.0932 mmol) of 3-amino-1,2,4-triazole (Atri), 0.216 g (2.0954 mmol) of 5-aminotetrazole monohydrate (Atet), 0.25 g (2.0987 mmol) of 1H-benzotriazole (Btri), or 0.142 g (2.0858 mmol) of imidazole (Imi). Then, 10 mL of ethanol was added to the solutions and stirring to around 3 hours at 80° C. After drying, 5 g of $SiO_2$ and 10 mL of water were added to the samples. The pH was adjusted to 10 with 0.1 M of NaOH, and the mixtures were heated to 70° C. Finally, the samples were washed and dried to obtain the products $SiO_2$-3GPS-Tri (Example Conjugate No. 1, herein "Conj. 1"), $SiO_2$-3GPS-Atri (Example Conjugate No. 2, herein "Conj. 2"), $SiO_2$-3GPS-Atet (Example Conjugate No. 3, herein "Conj. 3"), $SiO_2$-3GPS-Btri (Example Conjugate No. 4, herein "Conj. 4"), $SiO_2$-3GPS-Imi (Example Conjugate No. 5, herein "Conj. 5"). The synthesis pathway is symbolically depicted in the FIG. 2.

CHARACTERIZATION: A Fourier-transform infrared (FT-IR) spectrophotometer (PerkinElmer, USA) was employed to record FT-IR spectra of samples in the range of 400 to 4000 $cm^{-1}$ with a resolution of 4 $cm^{-1}$ at room temperature. The differences in spectral peaks of the Conj. 1, Conj. 2, Conj. 3, Conj. 4, Conj. 5 were then evaluated, as discussed below.

Thermogravimetric analysis (TGA) was conducted using a Perkin-Elmer, simultaneous thermal analyzer (STA6000, PerkinElmer, Ohio, USA). TGA data of Conj. 1, Conj. 2, Conj. 3, Conj. 4, Conj. 5 were obtained in the temperature range of 25° C. to 700° C., at the rate of 10° C./min, under inert environment ($N_2$ flow rate: 20 mL/min).

CANCER CELL TREATMENTS: Human colorectal carcinoma cells (HCT-116) cells were grown according to a method described in Khan, F. A.; Akhtar, S.; Almohazey, D.; Alomari, M.; Almofty, S. A.; Eliassari, A. "Fluorescent magnetic submicronic polymer (FMSP) nanoparticles induce cell death in human colorectal carcinoma cells" Artif *Artif. Cells, Nanomed., Biotechnol.* 2018, (doi: 10.1080/21691401.2018.1491476). HCT-116 cells were grown in Dulbecco Modified Eagle Medium (DMEM), 10% fetal bovine serum, L-glutamine, selenium chloride, penicillin, and streptomycin. The cells were cultured in a $CO_2$ incubator (Heracell 150i, Thermo-scientific, USA) at 37° C. under 5% $CO_2$ for 48 to 72 hours. Confluenced cells were seeded into 96-well cell plates and, once the cells became 80% confluenced, the cancer cells were treated with different concentrations (100 µg/mL, 500 µg/mL and 750 µg/mL) of Conj. 1, Conj. 2, Conj. 3, Conj. 4, Conj. 5 respectively. Thereafter, the treated cancer cells were microscopically observed after 24 and 48 hour intervals. Each sample was taken in triplicate to obtain a statistical analysis.

CANCER CELL MORPHOLOGY: After the treating the HTC-116 cells with Conj. 1, Conj. 2, Conj. 3, Conj. 4, Conj. 5, the cells were observed using an inverted microscope (TS100F Eclipse, Nikon, Japan) to evaluate the anatomical and morphological changes. Each sample was observed at 200-fold and 400-fold magnification.

CANCER CELLS VIABILITY BY MTT ASSAY: To examine effect of Conj. 1, Conj. 2, Conj. 3, Conj. 4, Conj. 5 on cancer cells, a 3-(4,5-dimethylthiazol-2-yl)-2,5-diphenyltetrazolium bromide (MTT) assay was conducted on the cells. The cancer cells were seeded at $6\times10^4$ cells/mL concentration in 96-well culture plates containing DMEM, 10% Fetal bovine serum, penicillin, and streptomycin and were incubated in $CO_2$ incubator until the cells were 80% confluenced. The cancer cells were then treated with Conj. 1, Conj. 2, Conj. 3, Conj. 4, Conj. 5 at concentrations of 1.3, 3.26, and 6.5 mg/mL, whereby no conjugate was added in the control groups. A 5.0 mg/mL MTT solution was added into each well, and the cells were again incubated for 4 hours in the $CO_2$ incubator and finally media was changed with the addition of DMSO. The samples were then measured using an ELISA plate reader (Biotek Instruments, USA) at wavelength 570 nm.

The following formula was used to calculate percentage of cell viability:

% of Cell viability=[Optical density (O.D) of Conj. 1, Conj. 2, Conj. 3, Conj. 4, or Conj. 5 cells]/[Optical density (O.D) of control cells]×100.

STATISTICAL ANALYSIS: The average (mean)±standard deviation (SD) from control and Conj. 1, Conj. 2, Conj. 3, Conj. 4, Conj. 5 treated groups were calculated. All statistical analyses were completed with GraphPad Prism 6 (GraphPad Software). The difference between control and Conj. 1, Conj. 2, Conj. 3, Conj. 4, Conj. 5 groups by a one-way ANOVA test (*$p<0.05$, $p<0.01$; *$p<0.001$) was taken as statistically significant.

After confirmation of the physical and structural properties of Conj. 1, Conj. 2, Conj. 3, Conj. 4, Conj. 5, by FT-IR, TGA, SEM, and TEM, the anti-cancer capabilities of these nanocomposites was tested. The results indicate that Conj. 1, Conj. 2, Conj. 3, Conj. 4, Conj. 5 have profound effects on cancer cell survivability. The microscopic evaluation demonstrates that Conj. 1, Conj. 2, Conj. 3, Conj. 4, Conj. 5 not only affected the (humna) cancer cell membrane, but also induced nuclear condensation, augmentation, and disintegration. Particularly, human colorectal carcinoma cells (HCT-116) were used to evaluate anti-cancer effects, and HCT-116 cells have been widely used for testing anti-cancer drugs and molecules.

Among the five exemplary nanocomposites tested, Conj. 1, Conj. 2, Conj. 3, Conj. 4, Conj. 5 are each highly effective in attenuating the cancer cells proliferation. Conj. 3 ($SiO_2$-3GPS-Atet) and Conj. 4 ($SiO_2$-3GPS-Btri) are more effective than Conj. 1 ($SiO_2$-3GPS-Tri), Conj. 2 ($SiO_2$-3GPS-Atri), and Conj. 5 ($SiO_2$-3GPS-Imi) in decreasing cancer cells proliferation. Derivatives such as 1,2,4-triazole, 3-aminotriazole, 5-aminotetrazole, imidazole are suitable candidates for azoles, or N-heterocyclic aromatic.

The effects of the exemplary conjugates was tested on cancer cells viability by staining with MTT. It was found that Conj. 1, Conj. 2, Conj. 3, Conj. 4, Conj. 5 treatments had dose dependent effects on cancer cells viability, verifying microscopically and by MTT analysis that inventive conjugates have potential in restricting cancer cell proliferation.

Nanocomposites within the scope of the invention (Conj. 1, Conj. 2, Conj. 3, Conj. 4, Conj. 5) decreased cancer cells proliferation in a concentration dependent manner, i.e., 1.3, 3.26, and 6.5 mg/mL dosages. For Conj. 5, the cancer cell viability was 71.17% of the control for 1.3 mg/mL, 62.22% of the control for 3.26 mg/mL, and 43.28% of the control for 6.5 mg/mL. Conj. 3 showed 56.80, 30.48, and 10.57% reductions. The Conj. 1 nanoparticles showed cancer viability 81.33, 70.57, and 40.62% less than the control, whereas for Conj. 2 showed 75.20, 52.53, and 40.62% decrease in cancer cells viability. For Conj. 4, the cancer cell viability was 76.44, 63.46, and 12.12% of the control. The most profound effects were observed with Conj. 3, followed by Conj. 4, where cancer cells survivability was respectively decreased to 10.57 and 12.12% of the control.

Referring now to the drawings, wherein like reference numerals designate identical or corresponding parts throughout the several views.

Figure 2:
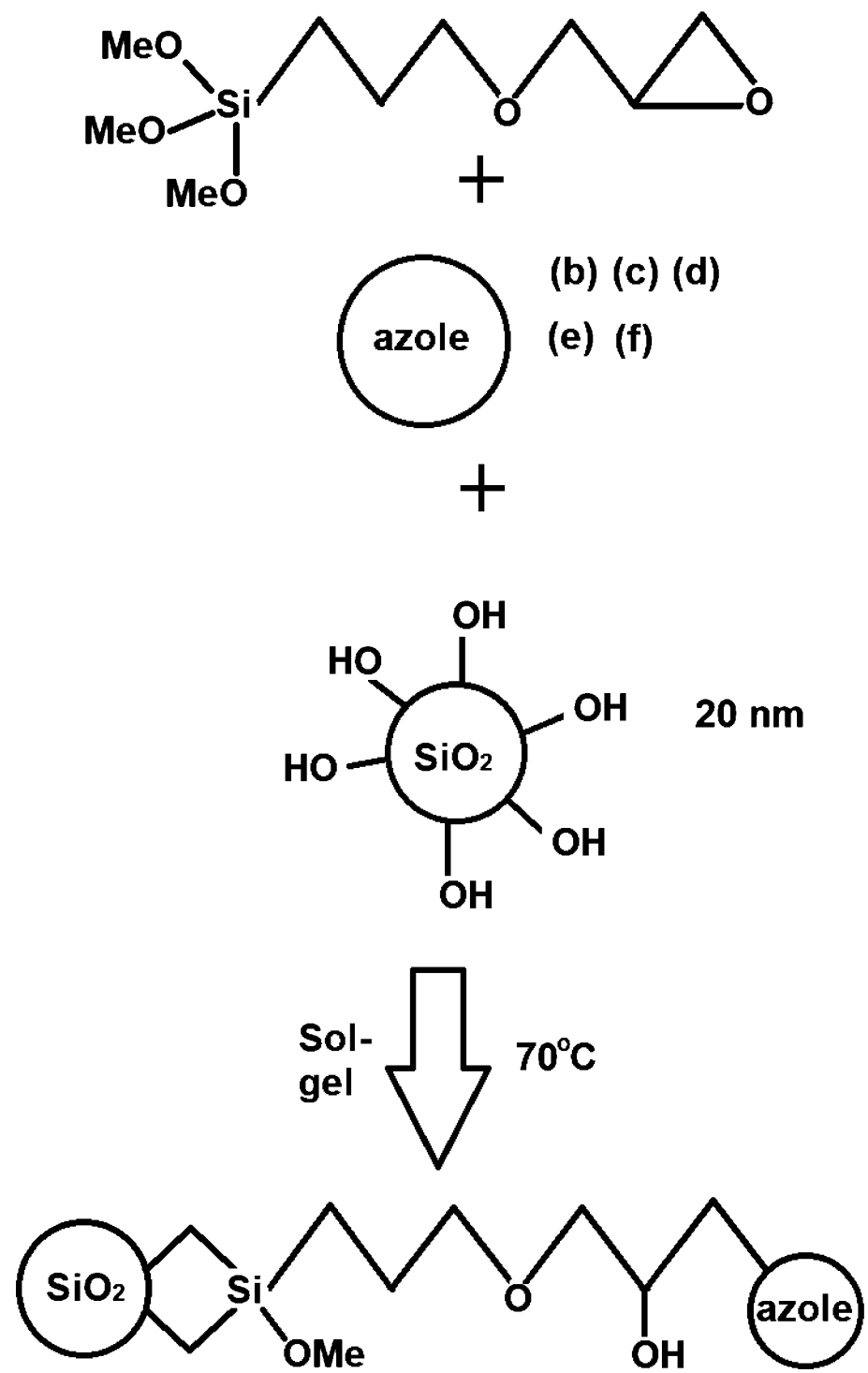
FIG. 2 shows an exemplary illustration of the synthetic pathway towards the conjugated nanosilica azole samples.

FIG. 1 shows the materials used in making exemplary suitable conjugates, and FIG. 2 shows a generalized theoretical synthetic representation of a manner of making inventive conjugates.

Figure 3:
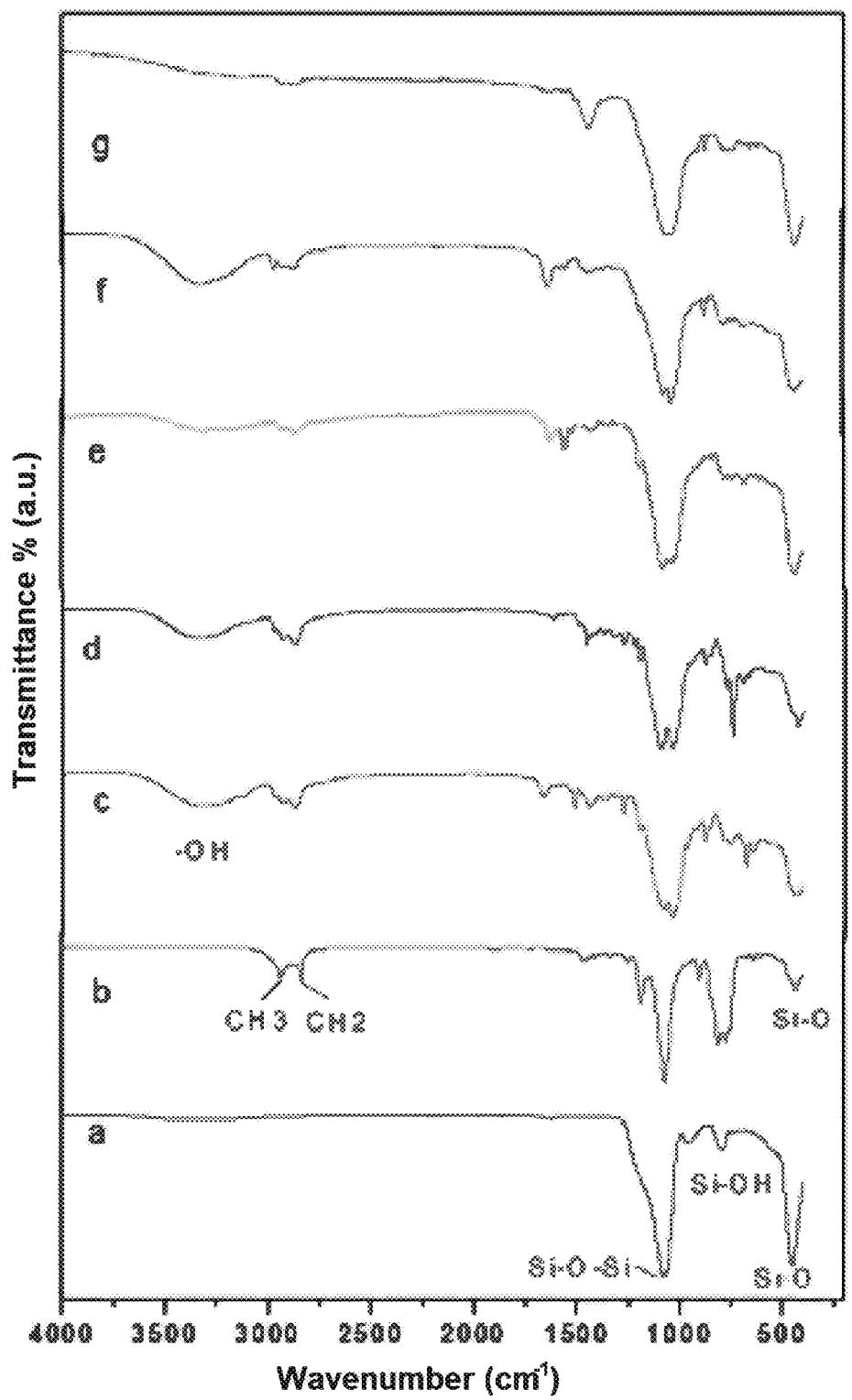
FIG. 3 shows FT-IR spectra of (a) $SiO_2$ nanoparticles, (b) 3-glycidyloxypropyl trimethoxysilane, (c) $SiO_2$-3GPS-Tri (Example Conjugate No. 1, hereinafter "Conj. 1"), (d) $SiO_2$-3GPS-Atri (Example Conjugate No. 2, hereinafter "Conj. 2"), (e) $SiO_2$-3GPS-Atet (Example Conjugate No. 3, hereinafter "Conj. 3"), (f) $SiO_2$-3GPS-Btri (Example Conjugate No. 4, hereinafter "Conj. 4"), (g) $SiO_2$-3GPS-Imi (Example Conjugate No. 5, hereinafter "Conj. 5"), with evident overlap in many functional groups of absorption frequencies and silica nanoparticle characteristic bands at 473 $cm^{-1}$ and 800 $cm^{-1}$ attributed to Si—O out of plane deformation and Si—O bending.

FIG. 3 shows FT-IR spectra of (a) $SiO_2$ nanoparticles, (b) 3-glycidyloxypropyl trimethoxysilane, (c) Conj. 1, (d) Conj. 2, (e) Conj. 3, (f) Conj. 4, (g) Conj. 5. The FT-IR in FIG. 3 show evident overlap in many functional groups of absorption frequencies and silica nanoparticle characteristic bands at 473 $cm^{-1}$ and 800 $cm^{-1}$ attributed to Si—O out of plane deformation and Si—O bending.

Absorption peaks at 956 $cm^{-1}$ can be assigned to Si—OH stretching, while Si—O—Si stretching shows up at 1090 $cm^{-1}$. For 3-glycidyloxypropyl trimethoxysilane, shown in FIG. 3 as spectrum (b), FTIR spectrum illustrated bands at 436 $cm^{-1}$ which may be assigned to the Si—O bond, while 800 $cm^{-1}$, 908.5 $cm^{-1}$, 1080 $cm^{-1}$, and 1450 $cm^{-1}$ correspond to the epoxide (oxirane) ring vibration.

In FIG. 3, spectrum (c), has a broad peak at 3318 $cm^{-1}$ which may be attributed to —OH which formed from the epoxide ring-opening, while the 1,2,4-triazol and —NH peaks were observed at 2919 $cm^{-1}$. The distinctive absorption peaks at 1662 and 1513 $cm^{-1}$ indicate a N=N and C=N stretching of the triazole. The peak at 1438 $cm^{-1}$ is associated with stretching in the azole ring. Likewise, spectra (d) and (e) in FIG. 3, for Conj. 2 and Conj. 3, illustrate an —OH band near 3316 $cm^{-1}$ that shifted to 3277 $cm^{-1}$ to 3-amino-1,2,4-triazole, whereas the peaks at 2880 and 2916 $cm^{-1}$ may be assigned to $CH_2$. Interestingly, the stretching vibrations of C=N disappeared completely (were not evident) for Conj. 2, but appeared for 5-aminotetrazole monohydrate at 1585 cm$^{-1}$. Additionally, a peak at 1461 cm$^{-1}$ corresponding to azolic ring was detected for Conj. 2 but shifted and was smaller (1436 cm$^{-1}$) for Conj. 3. A peak at 414 cm$^{-1}$ ascribed the Si—O bond shifted to 457 cm$^{-1}$ for Conj. 3.

FIG. 3, spectrum (f), shows broad peaks 3343 and 1637 cm$^{-1}$ indicating —OH and N═N ring stretching and the presence of 1H-benzotriazole, but, as seen in spectrum (g), these peaks disappear entirely for the imidazole conjugate (Conj. 5). Further differences include band shifts for the imidazole C═N (2860 cm$^{-1}$), aromatic ring (1434 cm$^{-1}$), and Si—O (450 cm$^{-1}$).

Figure 4:
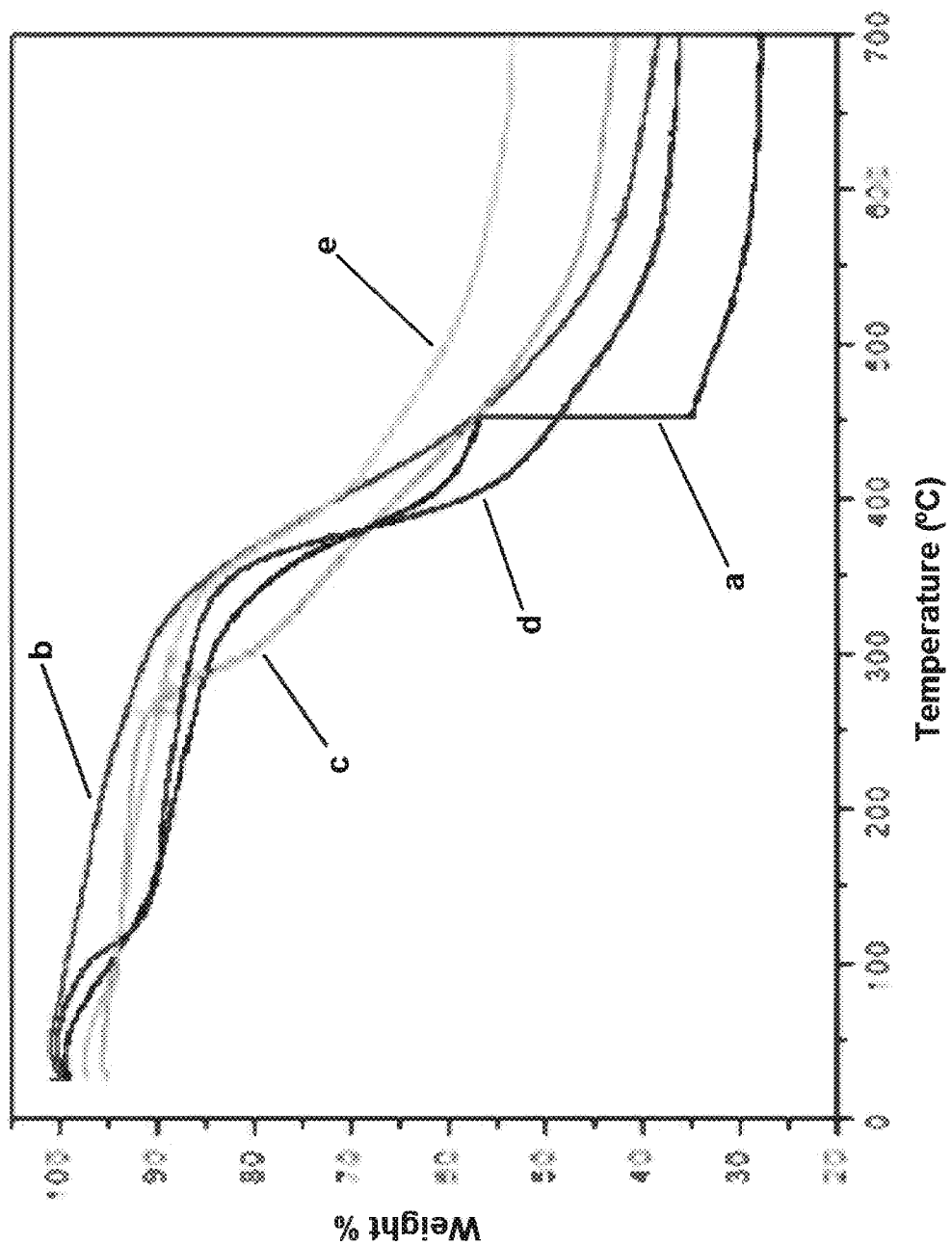
FIG. 4 shows thermogravimetric analysis (TGA) curves of (a) Conj. 1, (b) Conj. 2, (c) Conj. 3, (d) Conj. 4, and (e) Conj. 5.

FIG. 4 shows thermogravimetric analysis (TGA) curves of (a) Conj. 1, (b) Conj. 2, (c) Conj. 3, (d) Conj. 4, (e) Conj. 5. The TGA graphs depict simple and smooth plots of the thermal degradation of the samples. The TGA diagrams of weight loss versus temperature related to the polymer quantity in the conjugates. Degradation temperature is directly related to overall weight loss around 70 wt. % (Conj. 1), 62 wt. % (Conj. 2), 58 wt. % (Conj. 3), 64 wt. % (Conj. 4), and 47 wt. % (Conj. 5). The thermal decomposition of Conj. 4 (d) and Conj. 3 (c) respectively started at 139° C. and 250° C., while each of Conj. 1 (a), Conj. 2 (b), and Conj. 5 (e) began at approximately 320° C. The main weight loss occurred in each case at the interval of 250 to 450° C. presumably associated with deoxidative decomposition and corresponding to a weight loss of 20%. The third decomposition stage, from 450 to 500° C., may be associated the adjoining end groups and units and pyrolysis of organic chains. The final decomposition range, above 500° C., may be attributable to the thermal decomposition of silanol group before reaching thermal stability.

Figure 5A:
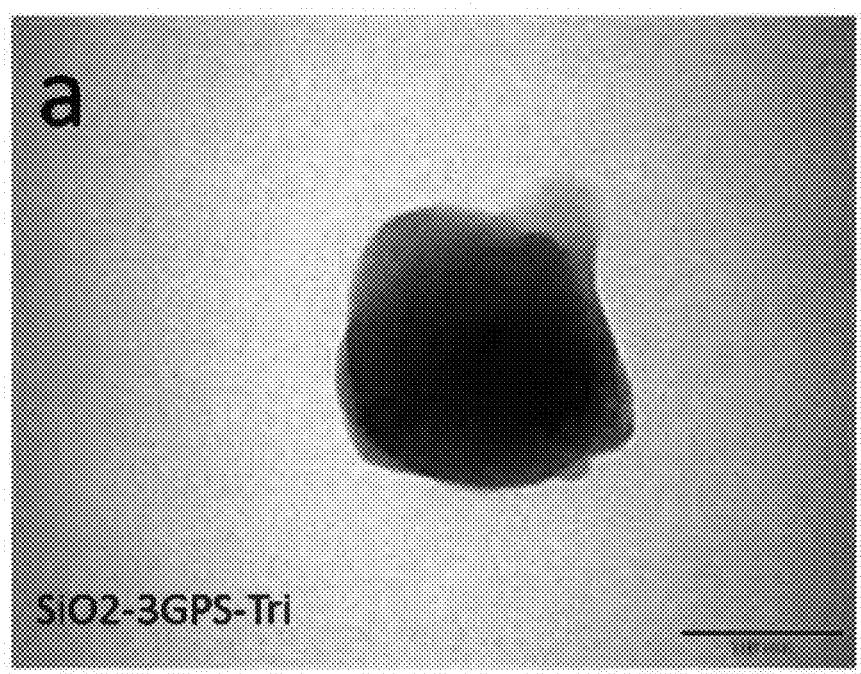
FIG. 5A shows a transmission electron microscope (TEM) image of Conj. 1 at a scale of 100 nm.
Figure 5B:
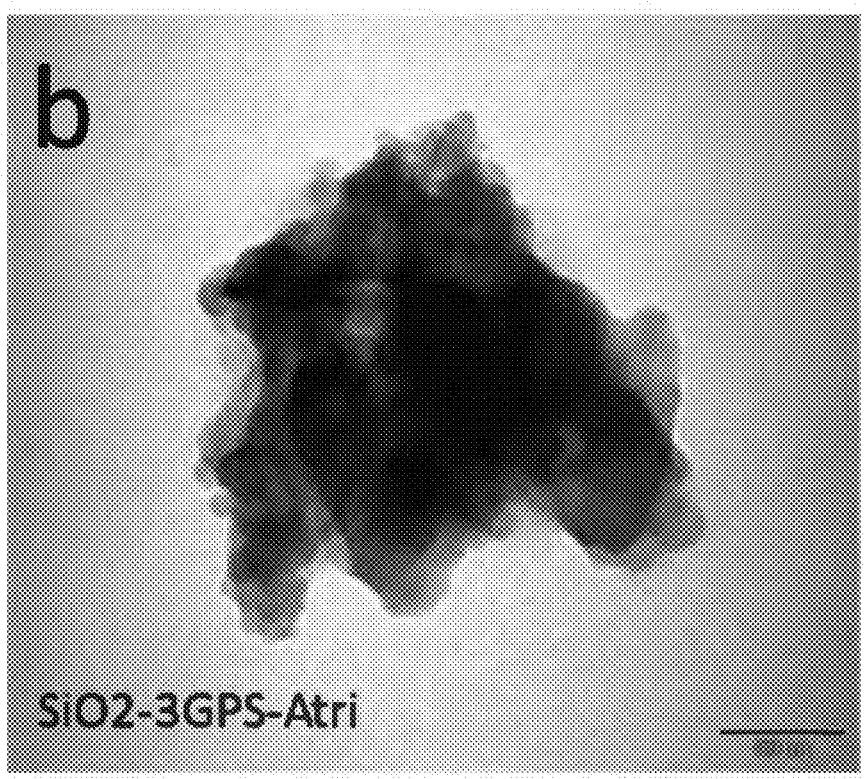
FIG. 5B shows a TEM image of Conj. 2 at a scale of 100 nm.

FIG. 5A to E show transmission electron microscope (TEM) images of (a) Conj. 1, (b) Conj. 2, (c) Conj. 3, (d) Conj. 4, and (e) Conj. 5 on a 100 nm scale. The particle size and morphology of nanoparticles noticeably changes with the azole used. As seen in FIG. 5A, the structure of Conj. 1 is almost uniform, with a diameter around 200 nm, which may manifest itself as average particle sizes in a range of from 150 to 250, 175 to 225, 180 to 220, 185 to 215, 190 to 210, or 195 to 205 nm, preferably with an aspect ratio in a rand of 1.25:1 to 1:1.25. In contrast, as seen in FIG. 5B, Conj. 2 has a more irregular shape, akin to a grape cluster, and a larger size, e.g., a longest dimension in a range of from 250 to 600, 300 to 550, or 350 to 500 nm, and/or at least 275, 325, 375, or 400 nm, preferably with an aspect ratio in a rand of 1.5:1 to 1:1.5.

Figure 5C:
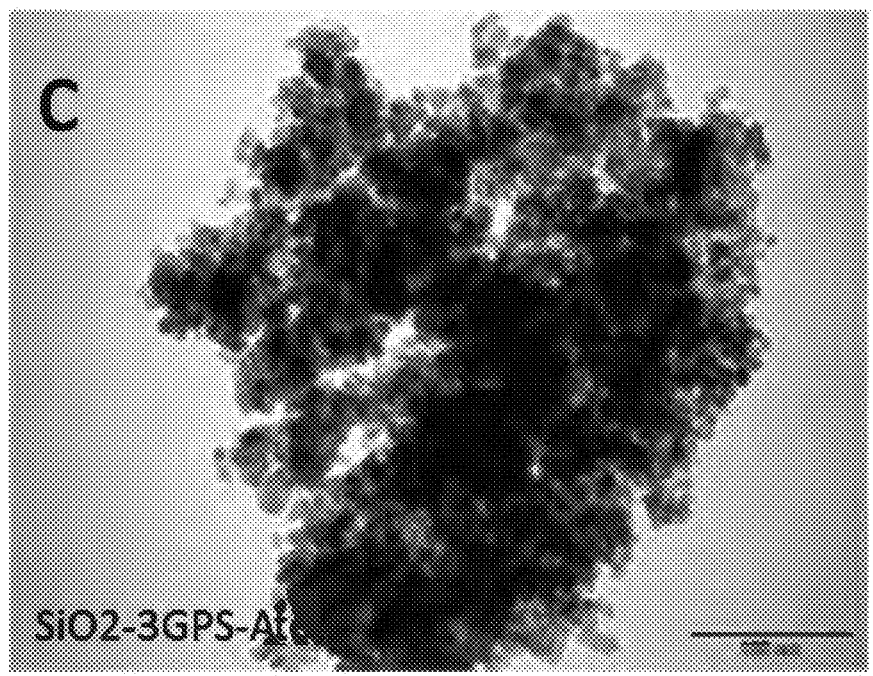
FIG. 5C shows a TEM image of Conj. 3 at a scale of 100 nm.
Figure 5D:
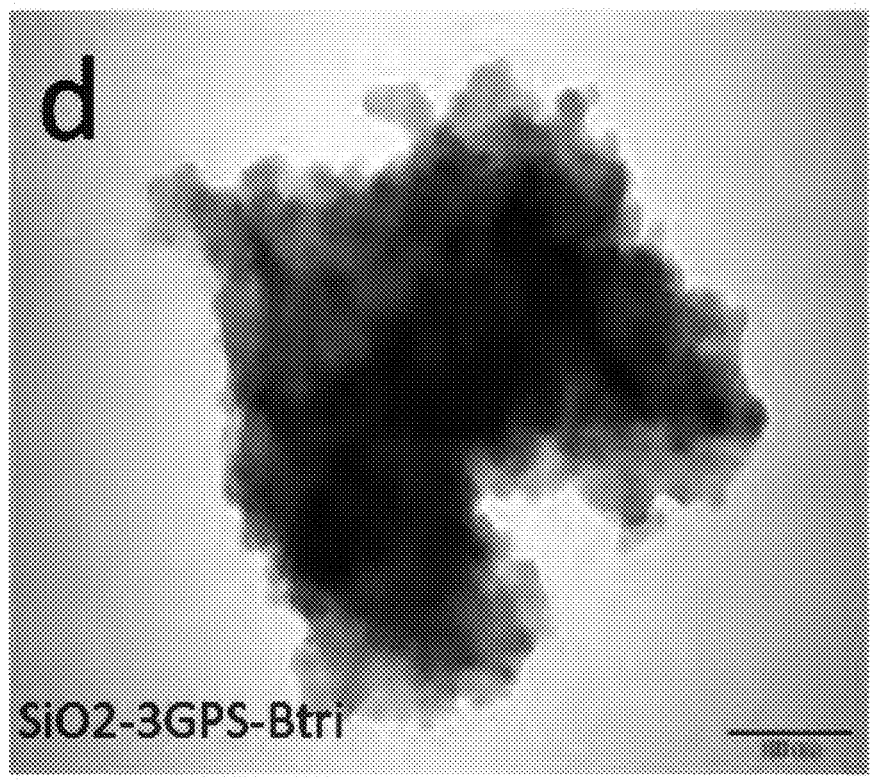
FIG. 5D shows a TEM image of Conj. 4 at a scale of 100 nm.
Figure 5E:
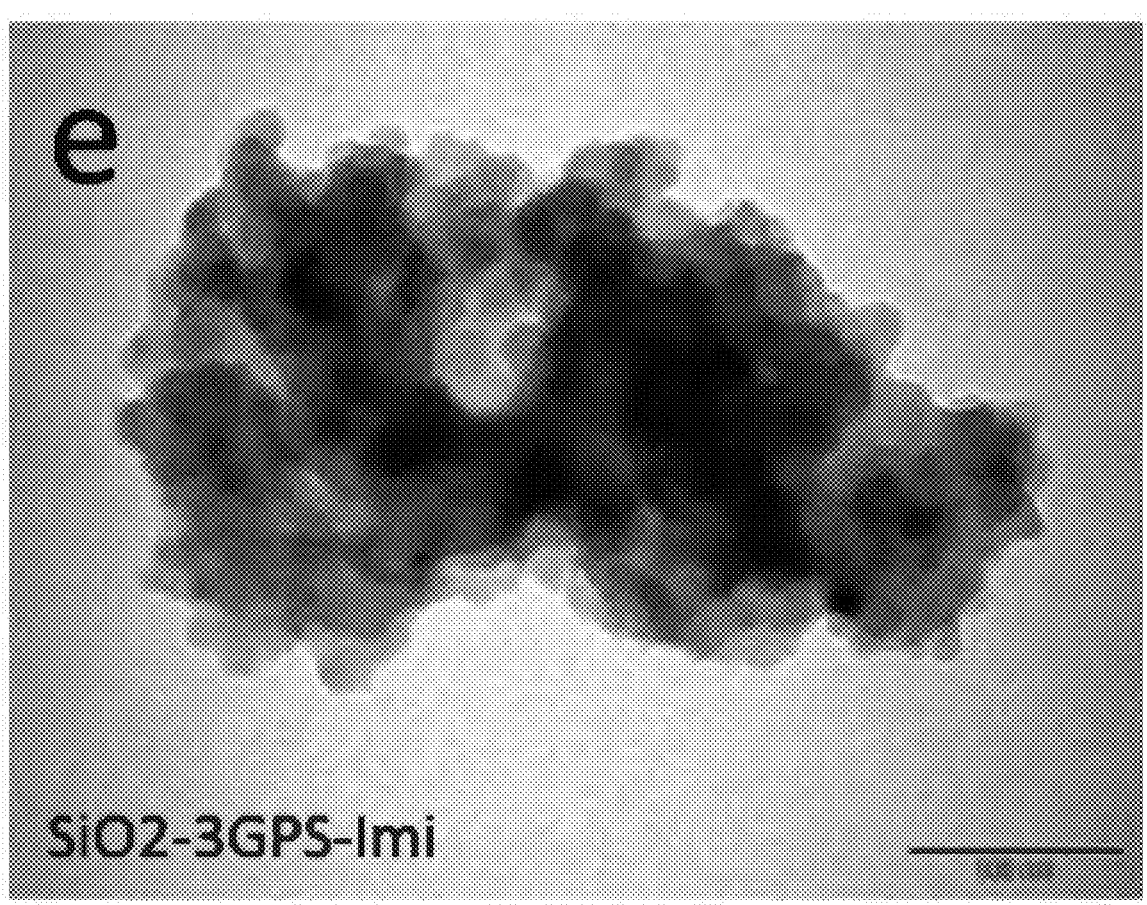
FIG. 5E shows a TEM image of Conj. 5 at a scale of 100 nm.
Figure 6A:
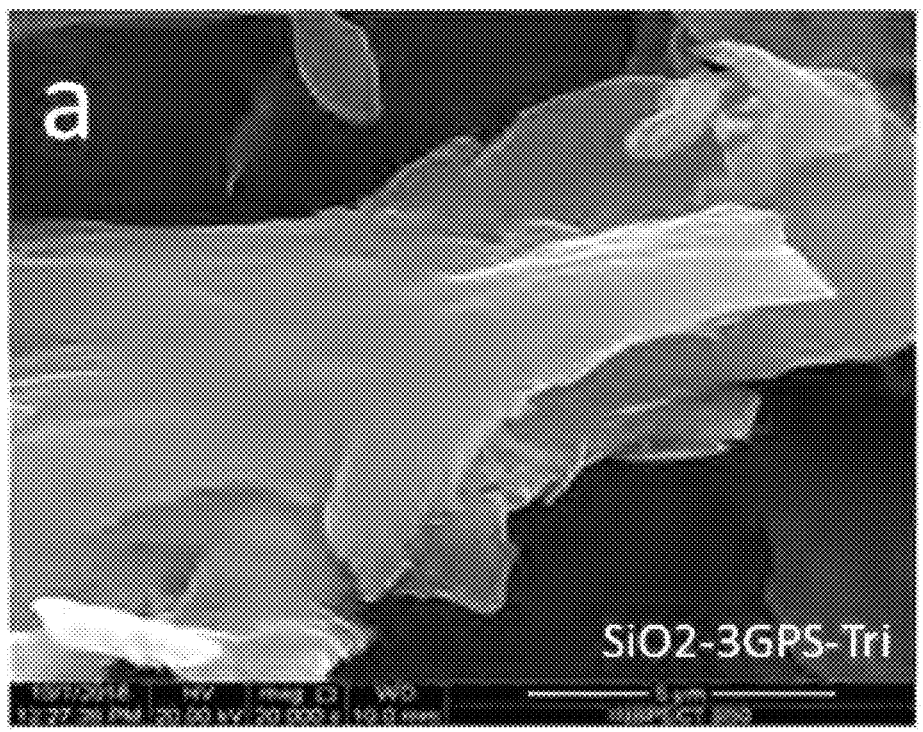
FIG. 6A shows a scanning electron microscope (SEM) image of Conj. 1 at a scale of 100 nm.
Figure 6B:
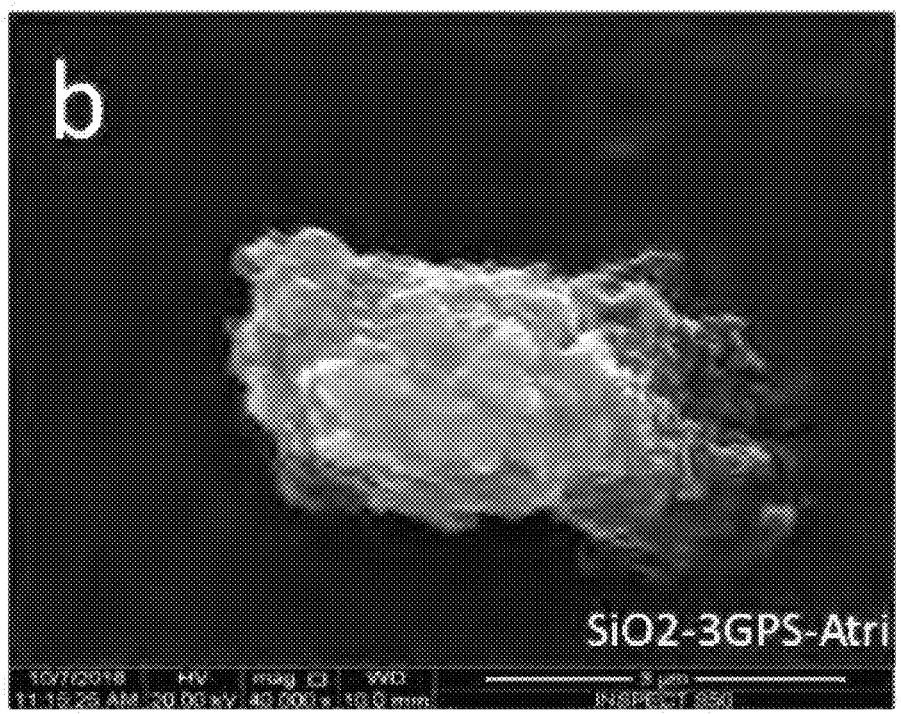
FIG. 6B shows an SEM image of Conj. 2 at a scale of 100 nm.
Figure 6C:
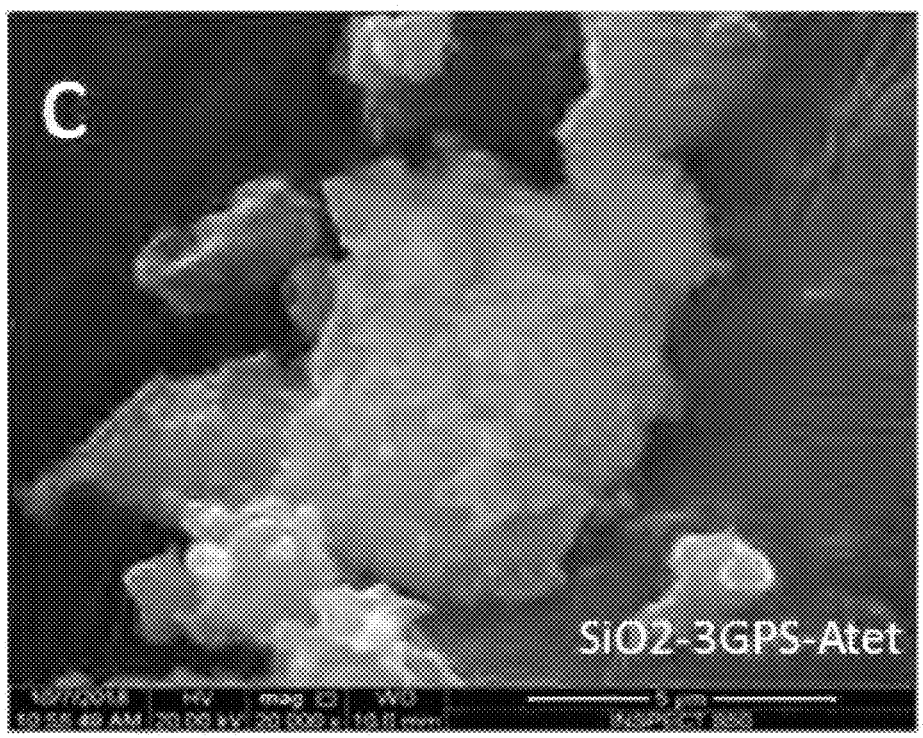
FIG. 6C shows an SEM image of Conj. 3 at a scale of 100 nm.
Figure 6D:
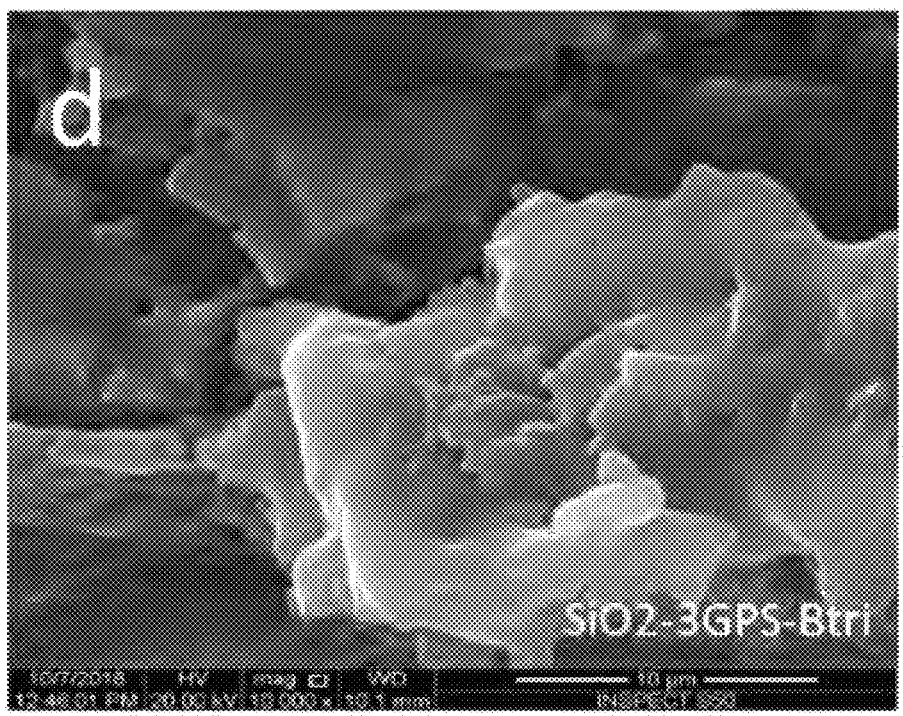
FIG. 6D shows an SEM image of Conj. 4 at a scale of 100 nm.
Figure 6E:
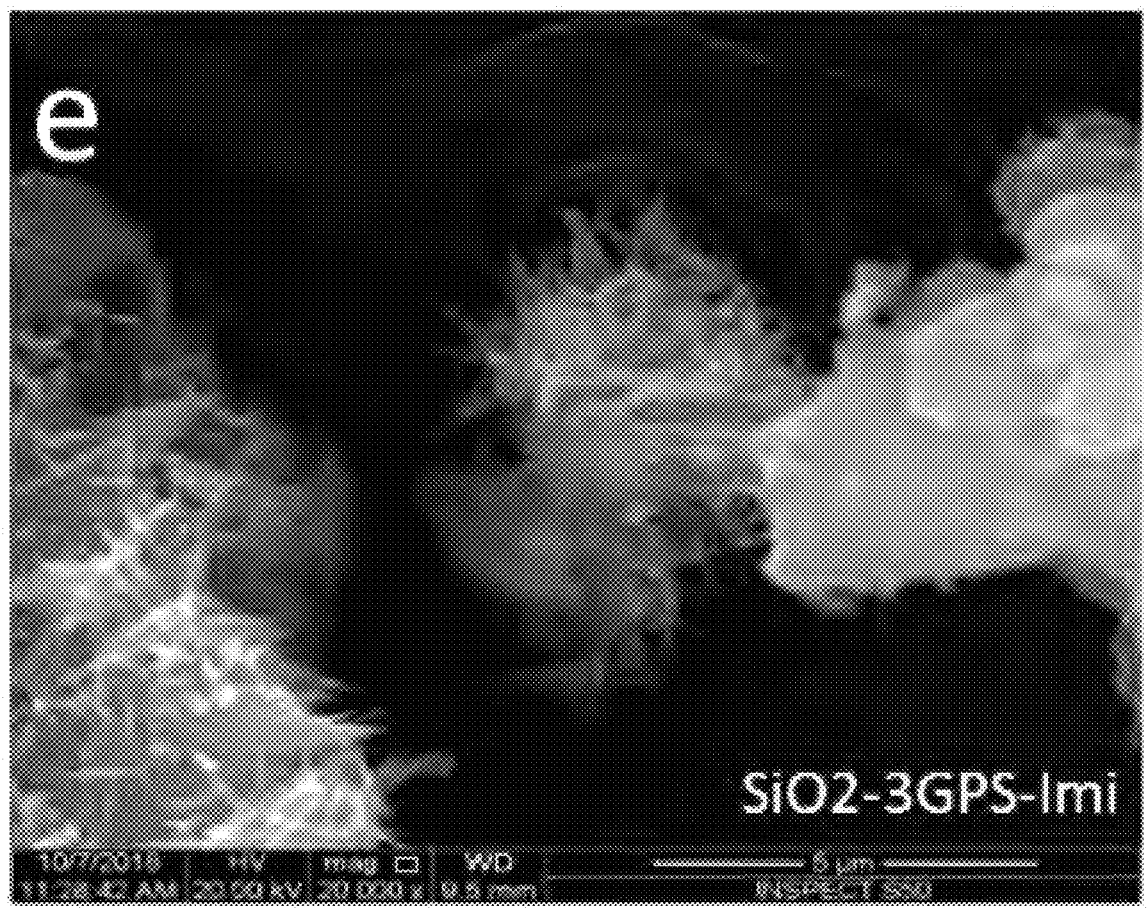
FIG. 6E shows an SEM image of Conj. 5 at a scale of 100 nm.

FIG. 5C shows a less closely agglomerated structure, indicating a higher disruption of nanoparticles in Conj. 3, giving it an appearance of dispersed caviar, due to the effect of 5-aminotetrazole on the structure. The agglomerations of Conj. 5C may have average largest dimensions of at least 500, 550, 600, 650, 700, 750, 800, 850, or 900 nm and/or no more than 2000, 1750, 1500, 1250, 1125, 1050, or 1000 nm, preferably with an aspect ratio in a rand of 2:1 to 1:2. As seen in FIGS. 5D and E, Conj. 4 and Conj. 5 have similar morphologies to each other and Conj. 3 (FIG. 5C) and comparable sizes, e.g., at least 500, 550, 600, 650, or 700 nm and/or no more than 1500, 1250, 1125, 1000, 900, 850, or 800 nm, in the longest dimension, preferably with an aspect ratio in a rand of 3:1 to 1:3. By comparing these TEM images, it is evident that the nanoarchitecture modified with different types of azoles.

FIG. 6A to E show scanning electron microscope (SEM) images of (a) Conj. 1, (b) Conj. 2, (c) Conj. 3, (d) Conj. 4, and (e) Conj. 5 on 100 nm scale. The SEM images in FIG. 6A to E confirm the aggregation of the conjugates and increases surface area of Conj. 1 (FIG. 6A), which shows the most plate-like structure, with the longest planar dimensions (e.g., at least 15, 20, 25, or 30 μm by at least 5, 7.5, 10, 12.5, or 15 μm), while Conj. 2 (FIG. 6B), Conj. 3 (FIG. 6C), and Conj. 4 (FIG. 6D), which show more rounded features and greater "z" directional dimensions, upon the planar central section. The planar sections of these conjugates may be at least 3, 5, 7.5, 10, 12.5, 15, 17.5, 20, 22.5 or 25 μm by 3, 5, 7.5, 10, 12.5, or 15 μm. Conj. 5 (FIG. 6E) shows synaptic (neuron-like) morphological features with sharp edges. Conj. 5 may have an average longest dimension in a range of from 5 to 100, 7.5 to 80, 10 to 60, or 12.5 to 50 μm.

Figure 7A:
FIG. 7A shows human colorectal carcinoma cells (HCT-116) cancer cell morphology after treatment by a control after 48 hours of treatment at 200× magnification.
Figure 7B:
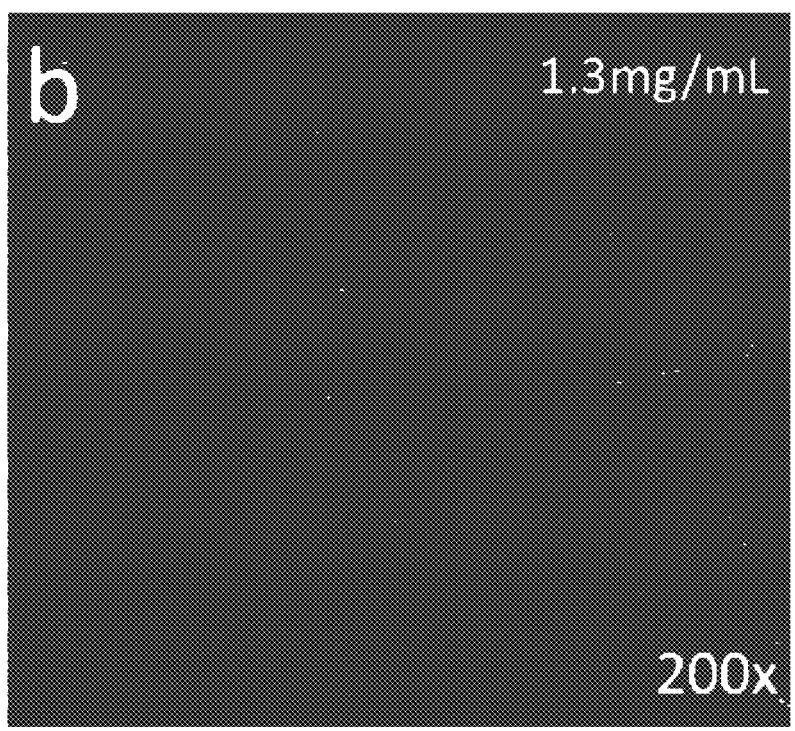
FIG. 7B shows HCT-116 cancer cell morphology after treatment by a dose of 1.3 mg/mL of Conj. 5 after 48 hours of treatment at 200× magnification.
Figure 7C:
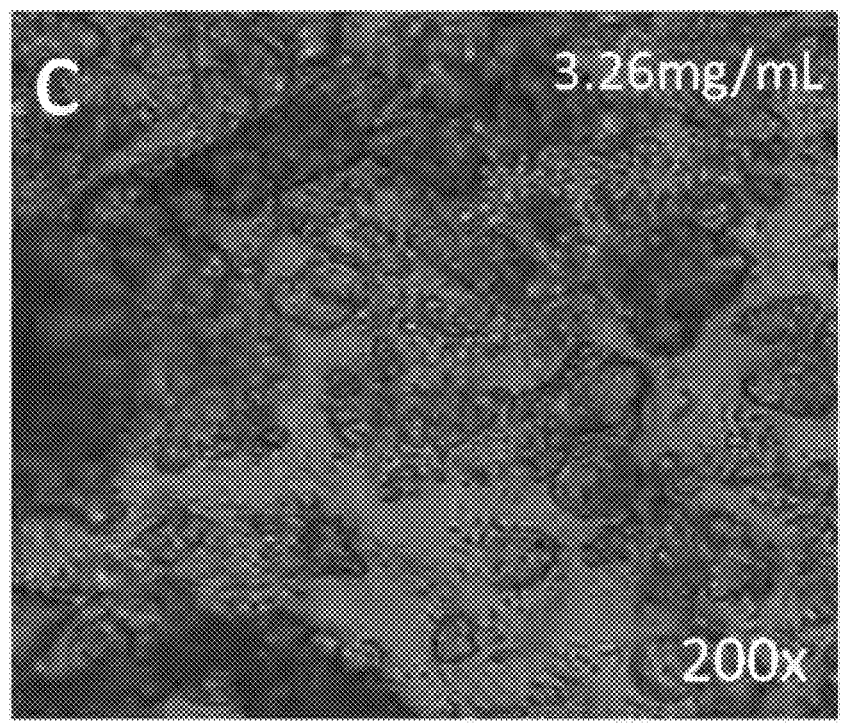
FIG. 7C shows HCT-116 cancer cell morphology after treatment by a dose of 3.26 mg/mL of Conj. 5 after 48 hours of treatment at 200× magnification.
Figure 7D:
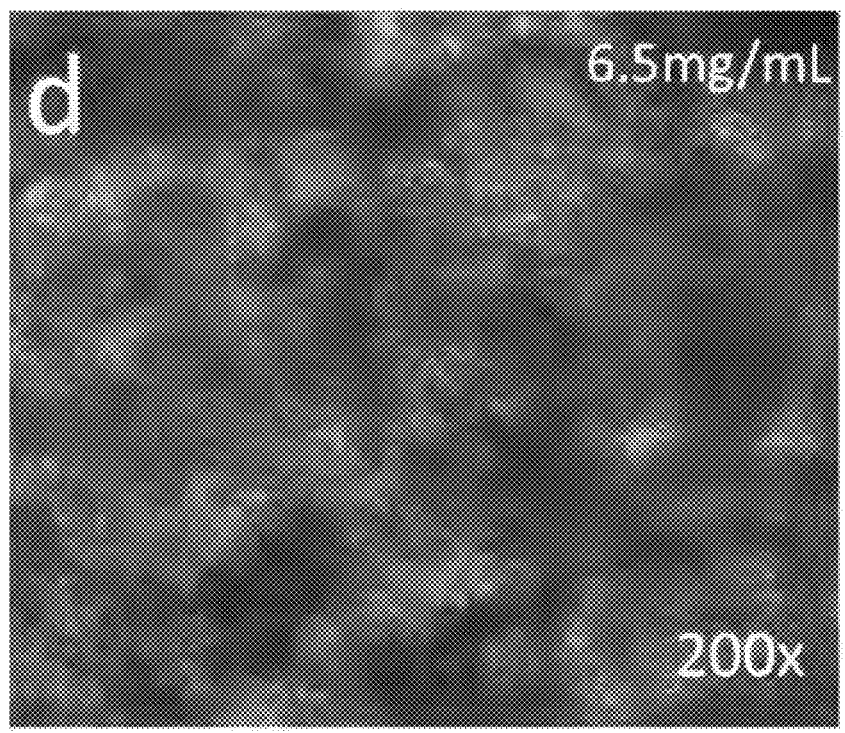
FIG. 7D shows HCT-116 cancer cell morphology after treatment by a dose of 6.5 mg/mL of Conj. 5 after 48 hours of treatment at 200× magnification.

FIG. 7A to D show cancer cell morphology of HCT-116 cells after treatment with a control without nanoparticles and in the growth media alone (FIG. 7A) or Conj. 5 at different concentrations for 48 hours at 200× magnification. FIG. 7B illustrates the results of HCT-116 cells treated with a dose of 1.3 mg/mL of Conj. 5. Post 48-hour treatment with SiO$_2$-3GPS-Imi (Conj. 5) at a dose of 1.3 mg/mL, illustrates high levels of nucleus condensation and nuclear augmentation of the HCT-116 cells (FIG. 7B) compared to the control (FIG. 7A). FIG. 7C shows the results of HCT-116 cells treated with a dose of 3.26 mg/mL of Conj. 5. The dose of 3.26 mg/mL (FIG. 7C) likewise showed strong nuclear condensation and augmentation and the beginning of cell membrane disruption and cell death. FIG. 7D shows the results of HCT-116 cells treated with a dose of 6.5 mg/mL of Conj. 5. The 6.5 mg/mL dose (FIG. 7D) showed a significant loss of cell population. The dose of 1.3 mg/mL, 3.26 mg/mL and 6.5 mg/mL showed strong nuclear condensation of complete cell bodies.

Figure 8A:
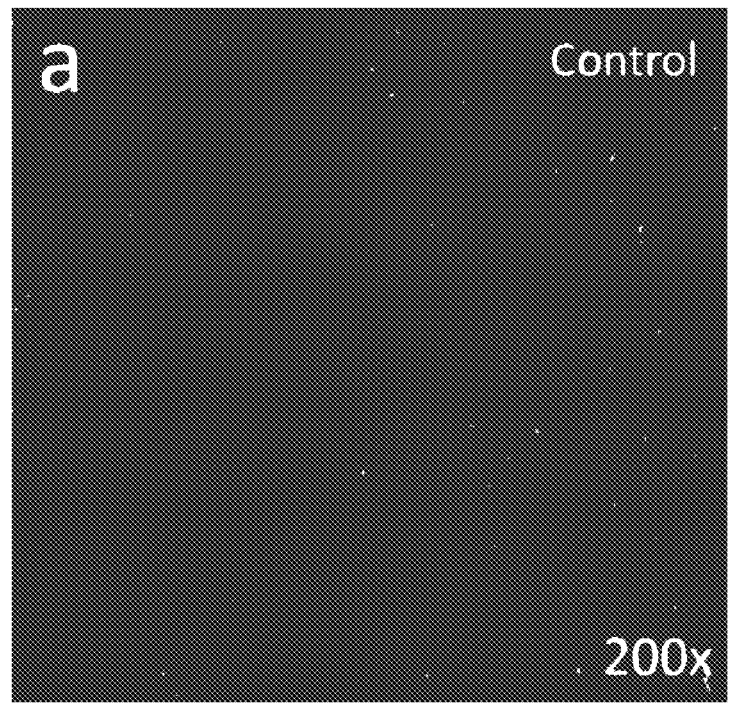
FIG. 8A shows HCT-116 cancer cell morphology after treatment by a control after 48 hours of treatment at 200× magnification.
Figure 8B:
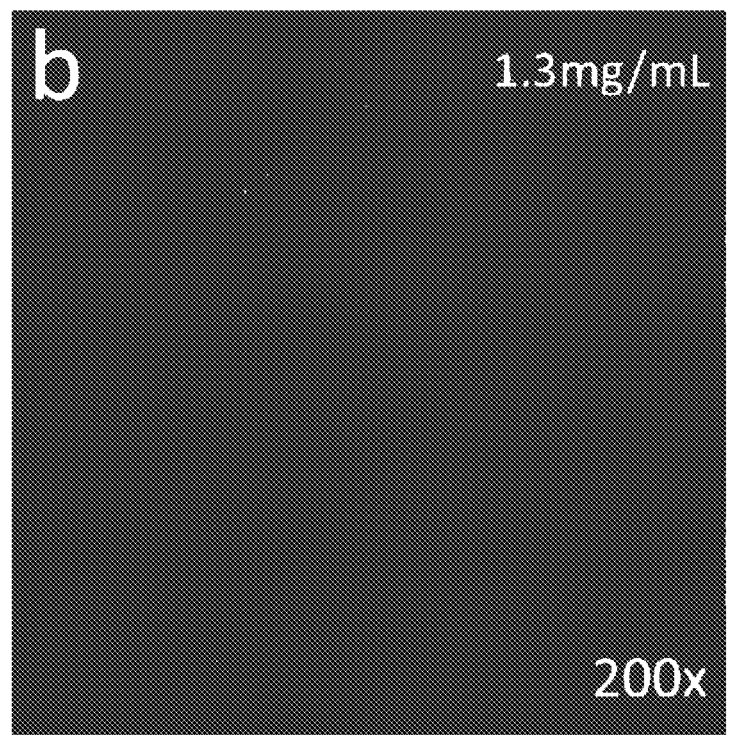
FIG. 8B shows HCT-116 cancer cell morphology after treatment by a dose of 1.3 mg/mL of Conj. 3 after 48 hours of treatment at 200× magnification.
Figure 8C:
FIG. 8C shows HCT-116 cancer cell morphology after treatment by a dose of 3.26 mg/mL of Conj. 3 after 48 hours of treatment at 200× magnification.
Figure 8D:
FIG. 8D shows HCT-116 cancer cell morphology after treatment by a dose of 6.5 mg/mL of Conj. 3 after 48 hours of treatment at 200× magnification.

FIG. 8A to D show cancer cell morphology of HCT-116 cells after treatment with a control (FIG. 8A) or Conj. 3 at different concentrations for 48 hours at 200× magnification. FIG. 8A is control and FIG. 8B to D show 1.3, 3.26, and 6.5 mg/mL Conj. 3 treatments, respectively. The doses of 1.3, 3.26, and 6.5 mg/mL all showed strong nuclear condensation of complete cell bodies. Post 48-hour treatment with SiO$_2$-3GPS-Atet (Conj. 3, FIG. 8B) at a dose of 1.3 mg/mL, showed significant levels of nucleus condensation and nuclear augmentation of the HCT-116 cells. No morphological changes were observed in control cells in FIG. 8A. The 3.26 mg/mL dose (FIG. 8C) showed nuclear condensation and augmentation of cancer cells, and the 6.5 mg/mL (FIG. 8D) dosage showed significant loss of cell population as large number of cancer cells were found dead.

Figure 9A:
FIG. 9A shows HCT-116 cancer cell morphology after treatment by a control after 48 hours of treatment at 200× magnification.
Figure 9B:
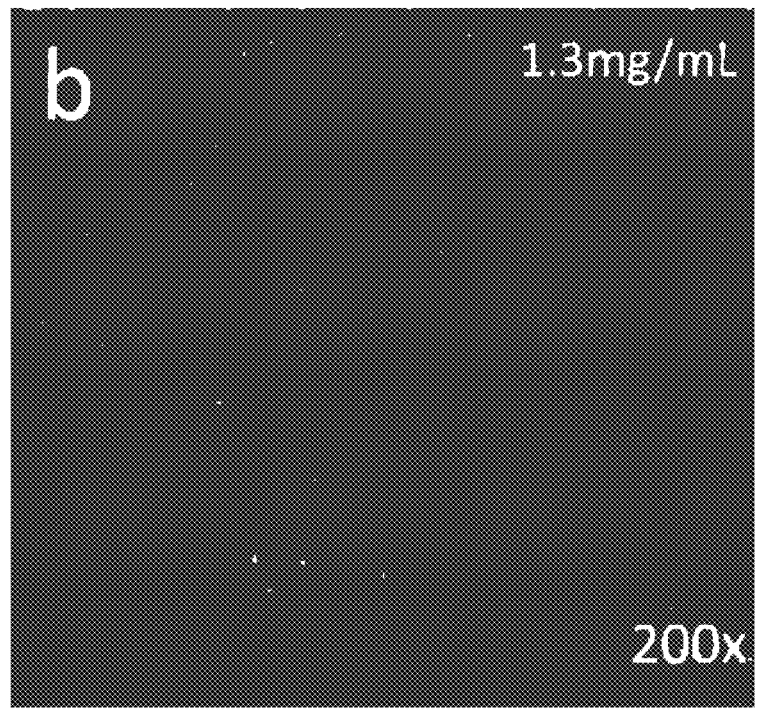
FIG. 9B shows HCT-116 cancer cell morphology after treatment by a dose of 1.3 mg/mL of Conj. 1 after 48 hours of treatment at 200× magnification.
Figure 9C:
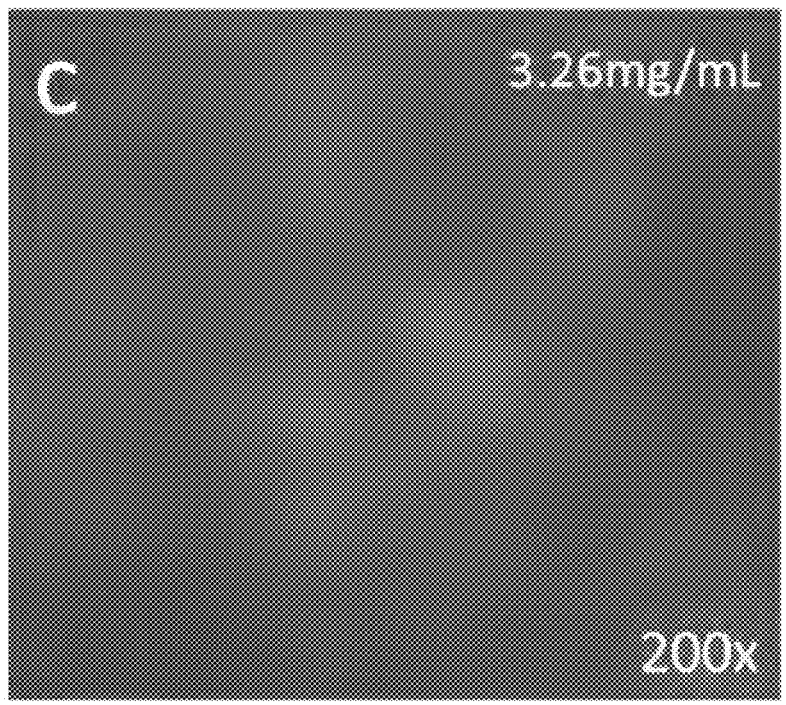
FIG. 9C shows HCT-116 cancer cell morphology after treatment by a dose of 3.26 mg/mL of Conj. 1 after 48 hours of treatment at 200× magnification.
Figure 9D:
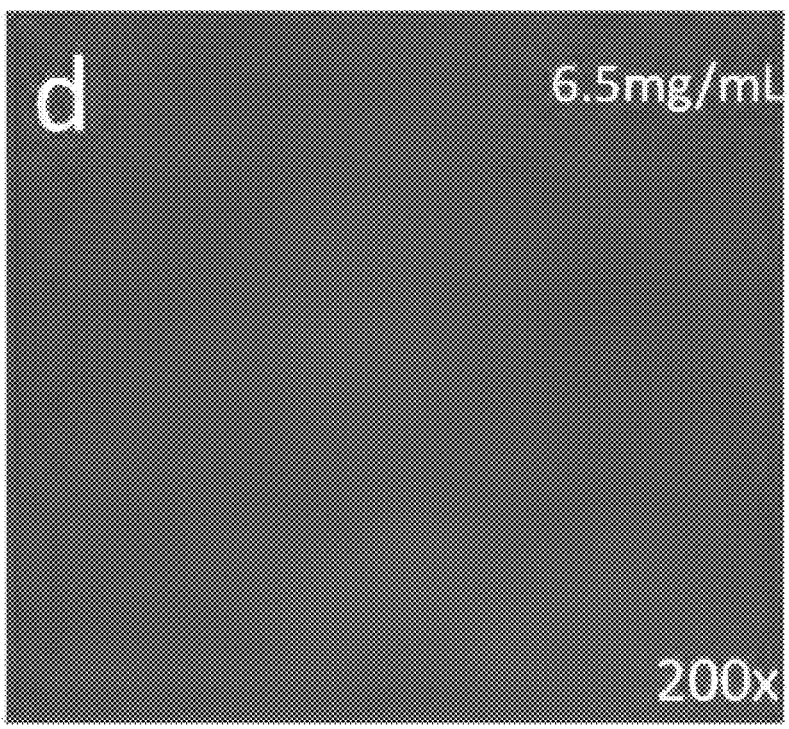
FIG. 9D shows HCT-116 cancer cell morphology after treatment by a dose of 6.5 mg/mL of Conj. 1 after 48 hours of treatment at 200× magnification.

FIG. 9A to D show cancer cell morphology of HCT-116 cells after treatment with a control (FIG. 9A) or Conj. 1 at different concentrations for 48 hours at 200× magnification. FIG. 9A is control and FIG. 9B to D show 1.3, 3.26, and 6.5 mg/mL Conj. 1 treatments, respectively. Post 48-hour treatment with SiO$_2$-3GPS-Tri (Conj. 1, FIG. 9B) at a dose of 1.3 mg/mL showed strong nucleus condensation and nuclear augmentation of the cancer cells. No morphological changes were observed in the control cells in FIG. 9A. The 3.26 mg/mL dose (FIG. 9C) showed further nucleus condensation and augmentation, and the 6.5 mg/mL dosage (FIG. 9D) showed a significant loss of cell population.

Figure 10A:
FIG. 10A shows HCT-116 cancer cell morphology after treatment by a control after 48 hours of treatment at 200× magnification.
Figure 10B:
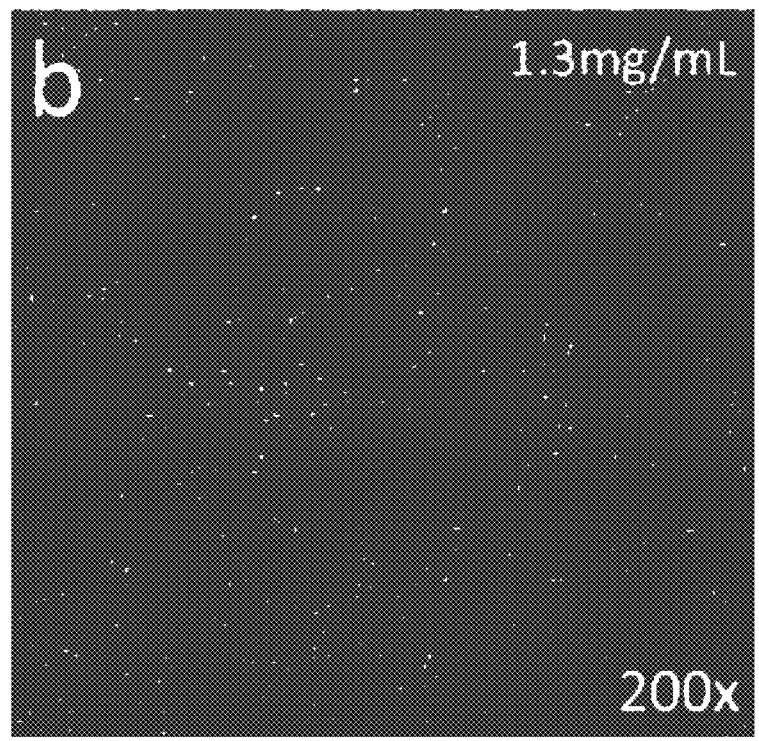
FIG. 10B shows HCT-116 cancer cell morphology after treatment by a dose of 1.3 mg/mL of Conj. 2 after 48 hours of treatment at 200× magnification.
Figure 10C:
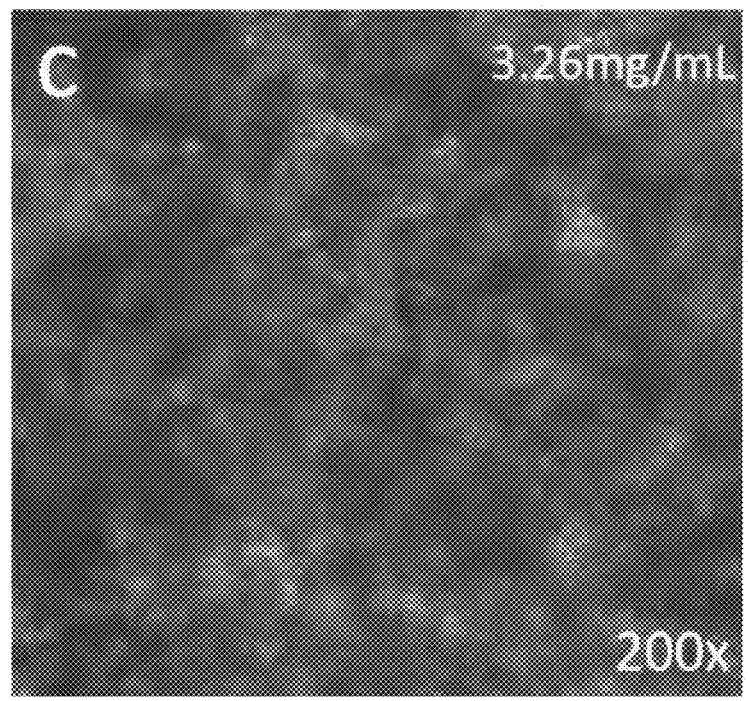
FIG. 10C shows HCT-116 cancer cell morphology after treatment by a dose of 3.26 mg/mL of Conj. 2 after 48 hours of treatment at 200× magnification.
Figure 10D:
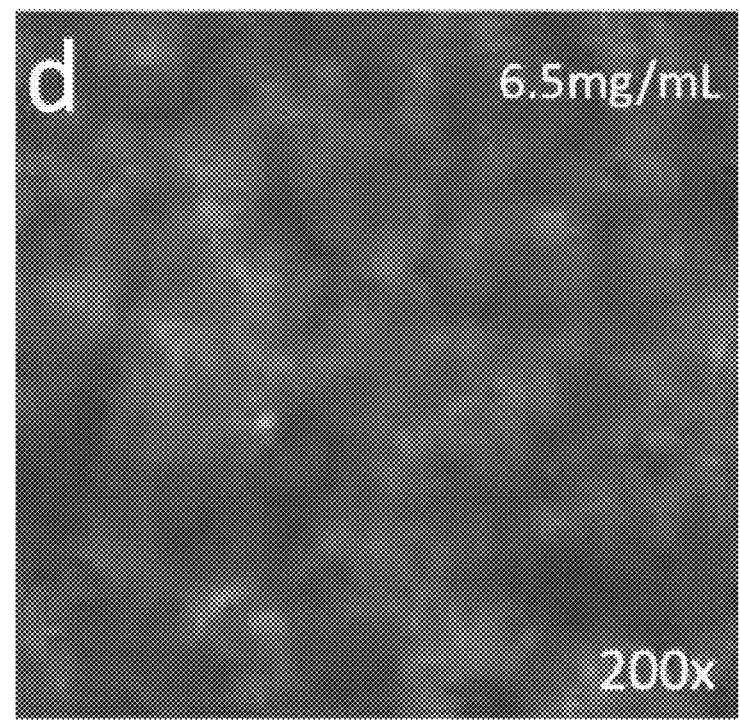
FIG. 10D shows HCT-116 cancer cell morphology after treatment by a dose of 6.5 mg/mL of Conj. 2 after 48 hours of treatment at 200× magnification.

FIG. 10A to D show cancer cell morphology of HCT-116 cells after treatment with a control (FIG. 10A) or Conj. 2 at different concentrations for 48 hours at 200× magnification. FIG. 10A is control and FIG. 10B to D show 1.3, 3.26, and 6.5 mg/mL treatments of Conj. 2, respectively. The 48 hour treatment of the HTC-116 cells with a 1.3 mg/mL dose of SiO$_2$-3GPS-Atri (Conj. 2, FIG. 10B) showed strong nucleus condensation and nuclear augmentation of the cancer cells.

No morphological changes were observed in the control cells, as seen in FIG. 10A. The dose of 3.26 mg/mL (FIG. 10C) showed further nucleus condensation and augmentation, and the 6.5 mg/mL dosage (FIG. 10D) showed a significant loss of cell population.

Figure 11A:
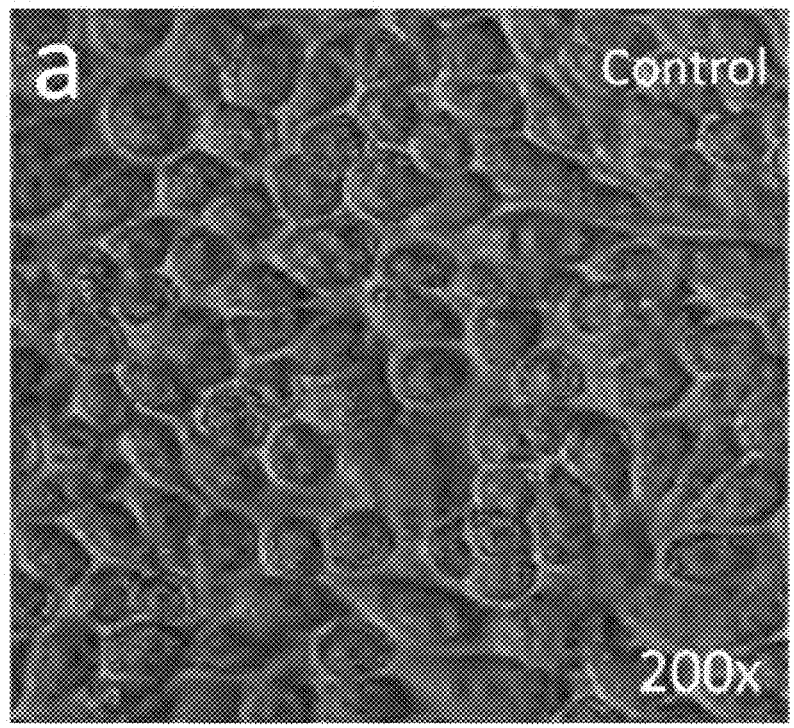
FIG. 11A shows HCT-116 cancer cell morphology after treatment by a control after 48 hours of treatment at 200× magnification.
Figure 11B:
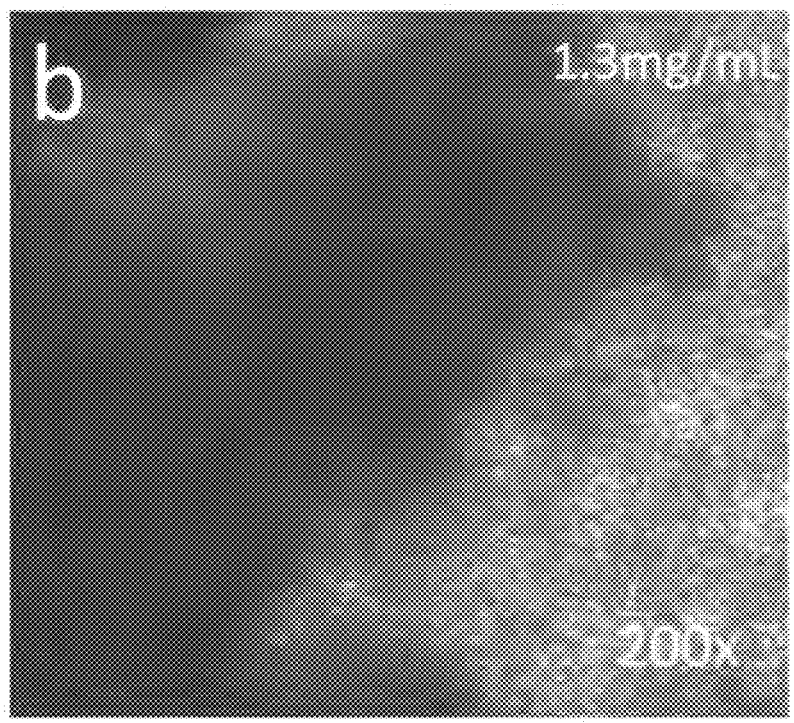
FIG. 11B shows HCT-116 cancer cell morphology after treatment by a dose of 1.3 mg/mL of Conj. 4 after 48 hours of treatment at 200× magnification.
Figure 11C:
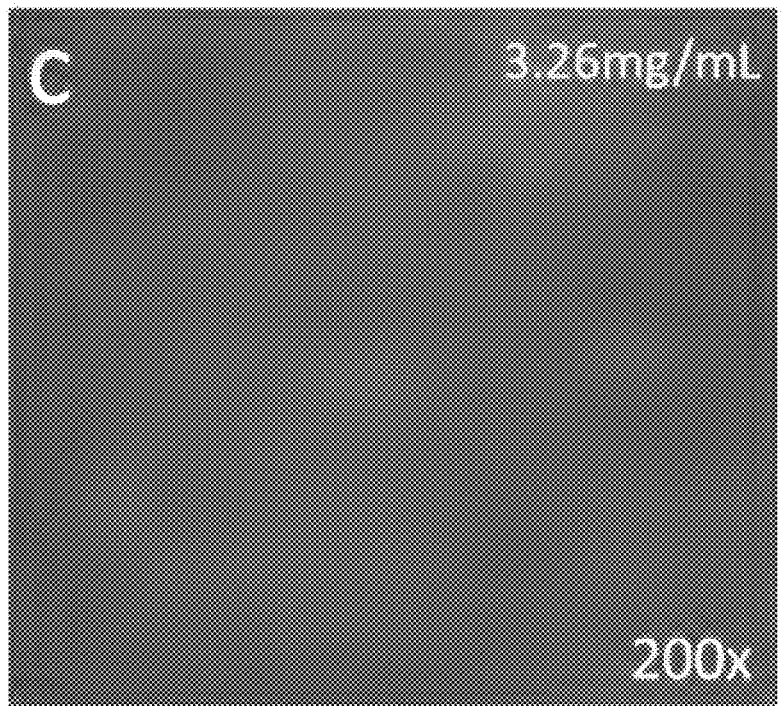
FIG. 11C shows HCT-116 cancer cell morphology after treatment by a dose of 3.26 mg/mL of Conj. 4 after 48 hours of treatment at 200× magnification.
Figure 11D:
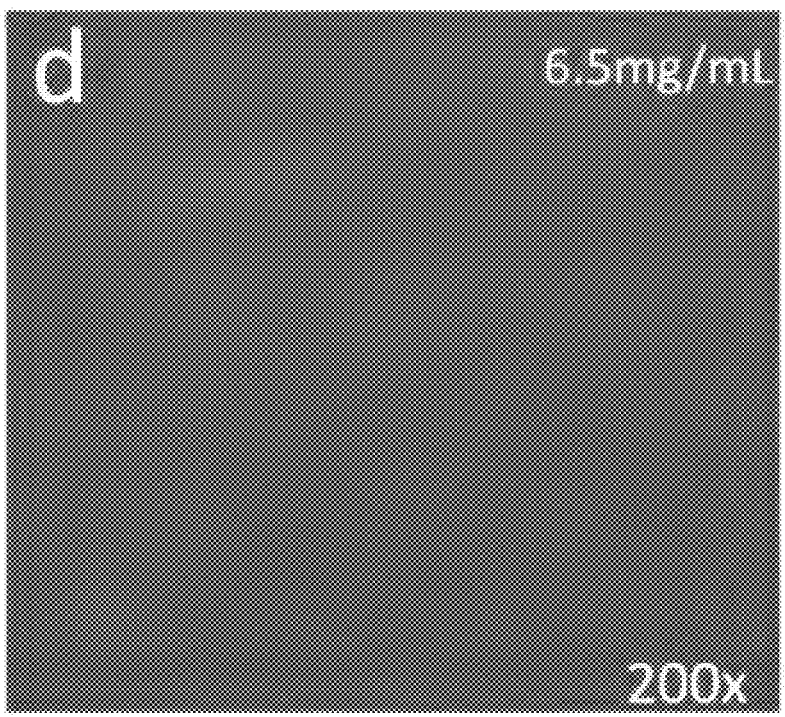
FIG. 11D shows HCT-116 cancer cell morphology after treatment by a dose of 6.5 mg/mL of Conj. 4 after 48 hours of treatment at 200× magnification.

FIG. 11A to D show cancer cell morphology of HCT-116 cells after treatment with a control (FIG. 11A) or Conj. 4 at different concentrations for 48 hours at 200× magnification. FIG. 11A is control and FIG. 11B to D show 1.3, 3.26, and 6.5 mg/mL treatments of Conj. 4, respectively. The 48 hour treatment of the HTC-116 cells with a 1.3 mg/mL dose of $SiO_2$-3GPS-Btri (Conj. 4, FIG. 11B) showed disintegration of cancer cell bodies compared to control cells (FIG. 11A). The dosages of 3.26 mg/mL and 6.5 mg/mL respectively showed strong nuclear condensation and augmentation in FIGS. 11C and D.

Figure 12:
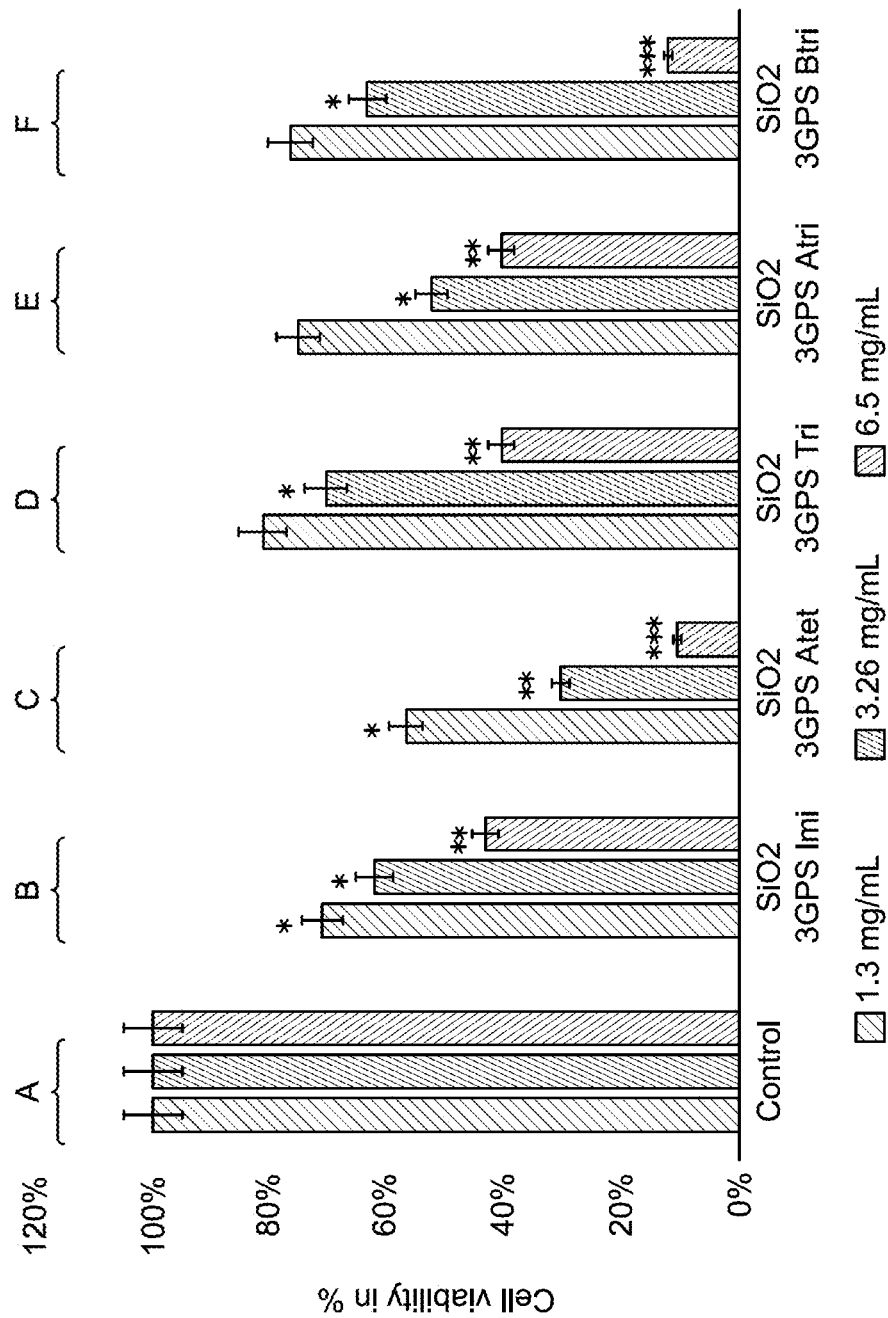
FIG. 12 shows cancer cell viability in a 3-(4,5-dimethylthiazol-2-yl)-2,5-diphenyltetrazolium bromide (MTT) assay using HCT-116 cells treated with a control, Conj. 4, Conj. 3, Conj. 1, Conj. 2, and Conj. 5 at concentrations of 1.3, 3.26, and 6.5 mg/mL for 48 hours.

FIG. 12 shows HCT-116 cancer cell viability by the 3-(4,5-dimethylthiazol-2-yl)-2,5-diphenyltetrazolium bromide (MTT) assay treating with a control (leftmost), Conj. 4 ($2^{nd}$ from left), Conj. 3 ($3^{rd}$ from left), Conj. 1 ($3^{rd}$ from right), Conj. 2 ($2^{nd}$ from right), and Conj. 5 (rightmost) at concentrations of 1.3, 3.26, and 6.5 mg/mL for 48 hours. The data provided in FIG. 12 are the means (i.e., average values)±standard deviations of three different experiments. Differences between two treatment groups were analyzed by a Student's t test where *p<0.05, p<0.01, and *p<0.001, where the p-values were calculated by the t-test. No changes were observed in the control group (under the bracket "A"), though Groups B, D, and E show significant decreases in cancer cell viability (e.g., no more than 50, 45, 40, 35, 33, 30, 25, 22.5, 20, or 15% of the cell viability of the control), and Groups C and F show more dramatic decreases in cancer cell viability (e.g., no more than 20, 15, 10, 7.5, 5, 4, 3, 2, 1, or 0.5% of the cell viability of the control).

The MTT assays examine cell viability and the inhibition rate of HCT-116 cell line. Using different concentrations akin to the experiments above, i.e., 1.3, 3.26, and 6.5 mg/mL dosages for 48 hours, cancer cell viability was calculated. For Conj. 5, the cancer cell viability was 71.17, 62.22, and 43.28% respectively. Conj. 3 showed 56.80, 30.48, and 10.57% reductions. The Conj. 1 nanoparticles showed cancer viability 81.33, 70.57, and 40.62% less than the control, whereas for Conj. 2 showed 75.20, 52.53, and 40.62% decrease in cancer cells viability. For Conj. 4, the cancer cell viability was 76.44, 63.46, and 12.12% of the control. The most profound effects were observed with Conj. 3, followed by Conj. 4, where cancer cells survivability was respectively decreased to 10.57 and 12.12% of the control.

Numerous modifications and variations of the present invention are possible in light of the above teachings. It is therefore to be understood that within the scope of the appended claims, the invention may be practiced otherwise than as specifically described herein.

The invention claimed is:

1. A conjugate compound, comprising, in reacted form: a silicon dioxide nanoparticle having a surface modified with a linker of Formula (1)

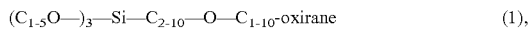

and an azole,
wherein the nanoparticle comprises at least 85 wt. % silica, based on total nanoparticle weight,
wherein, in the reacted form, the silicon of the linker forms a covalent bond to at least one of the oxygen atoms of the silicon dioxide of the nanoparticle, and
wherein the azole, in the reacted form, is covalently bonded with a carbon atom of the oxirane, in the reacted form, via ring-opening of the oxirane of the linker with the azole, as an optionally substituted hydroxymethine-methylene-azole unit.

2. The conjugate compound of claim 1, wherein the linker comprises, in reacted form, (3-glycidyloxypropyl)-trimethoxysilane and/or (3-glycidyloxypropyl)-triethoxysilane.

3. A composition comprising a plurality of conjugate compounds where each conjugate compound in the plurality of conjugate compounds is the conjugate compound of claim 1, wherein silicon dioxide nanoparticles of the plurality of conjugate compounds have an average particle size in a range of 5 to 60 nm.

4. The conjugate compound of claim 1, wherein the azole is 1,2,4-triazole, 3-amino-1,2,4-triazole, 5-aminotetrazole, 1H-benzotriazole, or imidazole.

5. The conjugate compound of claim 1, wherein the silicon dioxide nanoparticle is non-magnetic.

6. The conjugate compound of claim 1, wherein the silicon dioxide nanoparticle comprises at least 97.5 wt. % silica, relative to the total nanoparticle weight.

7. The conjugate compound of claim 1, which enhances cell death of cancer cells exposed to the conjugate, at least 50% relative to a placebo within 48 hours of exposure.

8. The conjugate compound of claim 7, wherein the cancer cells comprise HCT-116 cells.

9. The conjugate compound of claim 1, wherein the linker of Formula (1) has Formula (1a):

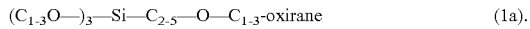

10. The composition of claim 3, wherein silicon dioxide nanoparticles of the plurality of conjugate compounds have a density in a range of from 2 to 3 g/mL at 25° C.

11. The composition of claim 3, wherein silicon dioxide nanoparticles of the plurality of conjugate compounds have a bulk density in a range of from 0.008 to 0.015 g/mL.

12. A therapeutic agent, comprising:
at least 50 wt. % of the conjugate compound of claim 1 relative to total agent weight,
wherein the agent is suitable to enhance cell death of cancer cells exposed to the agent, at least 50% relative to a placebo.

* * * * *